(12) United States Patent
Li et al.

(10) Patent No.: US 6,518,404 B1
(45) Date of Patent: Feb. 11, 2003

(54) HUMAN ENDOTHELIN-BOMBESIN RECEPTOR ANTIBODIES

(75) Inventors: Yi Li, Sunnyvale, CA (US); Craig A. Rosen, Laytonsville, MD (US); Chandrika Kumar, West Windsor, NJ (US)

(73) Assignees: Human Genome Sciences, Inc., Rockville, MD (US); Smithkline Beecham Corp., Philadelphia, PA (US)

( * ) Notice: Subject to any disclaimer, the term of this patent is extended or adjusted under 35 U.S.C. 154(b) by 0 days.

(21) Appl. No.: 09/520,210

(22) Filed: Mar. 7, 2000

Related U.S. Application Data

(60) Division of application No. 09/030,970, filed on Feb. 26, 1998, now Pat. No. 6,143,519, which is a division of application No. 08/465,687, filed on Jun. 6, 1995, now Pat. No. 5,750,370, which is a continuation-in-part of application No. PCT/US94/11843, filed on Oct. 17, 1994.

(51) Int. Cl.[7] ............................................. C07K 16/28
(52) U.S. Cl. ............................... 530/387.9; 530/388.1; 530/387.1; 530/387.3; 530/388.15; 530/389.1
(58) Field of Search ........................... 530/387.1, 388.1, 530/387.3, 387.9, 388.15, 389.1

(56) References Cited

U.S. PATENT DOCUMENTS 5,260,273 A * 11/1993 Cochrane ..................... 514/12

FOREIGN PATENT DOCUMENTS

| EP | 522868 | 1/1993 |
| WO | WO 90/11297 | * 10/1990 |

OTHER PUBLICATIONS

Corjay, et al., "Two Distinct Bombesin Receptor Subtypes Are Expressed and Functional in Human Lung Carcinoma Cells," *J. Biol. Chem.*, 266(28):18771–18779 (Oct. 05, 1991).
Hosoda et al., "Targeted and Natural (Piebald–Lethal) Mutations of Endothelin–B Receptor Gene Produce Megacolon Associated with Spotted Coat Color in Mice," *Cell*, 79:1267–1276 (Dec. 30, 1994) Cell Press.
Hori, et al., "Distinct Tissue Distribution and Cellular Localization of Two Messenger Ribonucleic Acids Encoding Different Subtypes of Rat Endothelin Receptors," *Endocrinology*, 130(4):1885–1895 (1992).
Geneseq Accession No. Q39831 (May 20, 1993).
Geneseq Accession No. Q59243 (Mar. 16, 1994).
Genbank Accession No. M62108 (May 26, 1992).
Adachi et al., "Cloning and Characterization of cDNA Encoding Human A–Type Endothelin Receptor," *Biochem & Biophys Res. Comm.*, 180(3):1265–1272 (Dec. 14, 1991) Academic Press.
Arai et al., "Cloning and expression of a cDNA encoding an endothelin receptor," *Nature*, 348:730–732 (1990).
Elshourbagy et al., "Molecular cloning & characterization of the major endothelin receptor subtype in porcine cerebellum," *Mol. Pharma.*, 41:465–473 (1991).
Hayzer et al., "Cloning and Expression of a Human Endothelin Receptor: Subtype A," *Amer. J. Med. Sci.*, 304(4):231–238 (Oct. 1992).
Hosoda et al., "Cloning and expression of human endothelin–1 receptor cDNA," *FEBS*, 287(1,2):23–26 (1991), Elsevier Science Publishers B.V.
Miller et al., *TIPS*, 14:54–60 (1993).
Sakurai et al., "Cloning of a cDNA encoding a non–isopeptide–selective subtype of the endothelin receptor," *Nature*, 348:732–735 (1990).
Zachary et al., "Identification of a Receptor for Peptides of the Bombesin Family in Swiss 3T3 Cells by Affinity Cross–linking," *J. Biol. Chem.*, 262(9):3947–3950 (1987).
Genesq Accession No. Q39845 (Jan. 1993) Adams et al., "Expressed Sequence Tag human gene marker EST00359".
Genbank Accession No. R66426 (May 30, 1991) Hillier et al., "yh01b08.s2 Soares infant brain 1NIB *Homo sapiens* cDNA clone".
Genbank Accession No. H59604 (Oct. 06, 1995) Hillier et al., "yr 35b02.s1 Soares fetal liver spleen 1NFLS *Homo sapiens* cDNA clone".

* cited by examiner

*Primary Examiner*—Lorraine Spector
*Assistant Examiner*—Eliane Lazar-Wesley
(74) *Attorney, Agent, or Firm*—Human Genome Sciences, Inc.

(57) ABSTRACT

A human endothelin-bombesin receptor polypeptide and DNA (RNA) encoding such polypeptide and a procedure for disclosed. Also disclosed are methods for utilizing such polypeptide for identifying agonists and antagonists to such polypeptide. Agonists to the endothelin-bombesin receptor polypeptide of the present invention may be used to treat asthma, Parkinson's Disease, acute heart failure, hypotension and osteoporosis. Antagonists against such polypeptides may be used therapeutically to treat hypertension, ulcerigenesis, subarachnoid hemorrhage, asthma, tumors, ciclosporin toxicity, cancer and septic shock. Also disclosed are diagnostic methods for detecting mutations in the polynucleotides of the present invention and for detecting levels of the soluble polypeptides in samples derived from a host.

144 Claims, 21 Drawing Sheets

FIG. 1A

```
         10                    30                    50
          .                     .                     .
CCCACTATGTTGGCCAGGATGGTCTTGATTTCTTGACCTGTGTCTGCCCGCCTCTACC
                70                    90                   110
                 .                     .                     .
TCCCAAAGTGCCGGGATTACAGGCGTGACTGCTGTGCCCGGCCCCAGCATCACTTTTATA
          130                   150                   170
           .                     .                     .
GCTTTCTGTGCCTCTCTTCCTCTGGGCCTTGGTTATGAAGCCACTTGCCTTTCTCTGTTGG
                190                   210                   230
                 .                     .                     .
GAAGCGAGCAGAATCAGATTGCTACTCATGATGCAGTCCGGCAGGGCATACTGTCACCT
          250                   270                   290
           .                     .                     .
TTGGCTGTGGACACAGTGTCAGGATAGGGGAGAAGCCCTTTAGTCCGTCTCTTCTTGACA
                310                   330                   350
                 .                     .                     .
CAGCCCCTCCTACCCTGGTTACGCTGGTGCTTCGCTTGGTTTAGAACAACCAAGACACTGA
          370                   390                   410
           .                     .                     .
GAATTATGCTGTCCTCAGAATGTCTGATGAAAGAACAGATTCACTTTTTGGACACAATG
                430                   450                   470
                 .                     .                     .
CCCATTAGCCATCTTTGGCAGTGTTTCTGATCAAAGGTTCCCCATGCCTGCTCTAGGAAA
          490                   510                   530
           .                     .                     .
GTAAACTTTTTCAGAATAAATCCTCAAATGGATTACTGAGTAGTCTTTGCACCATTCCC
                550                   570                   590
                 .                     .                     .
ATCAGCCTAATCAGACTGAATGGTCACGCTCAGTGCAAAAAGCTGTTTTGCTGTTAGGAT
```

FIG. 1B

```
610             630             650
GTTTCAGTGTTTCTGTCTTTCCTGGAACAGTTCAGTTGTTAAATTAGTAATTCAATC
        670             690             710
CTGACCAGTGTAAACCCACTTAATTATTGCAGCCTAAAGAATTCAGCTACTTCTACTCTT
        730             750             770
CATAAATGTGCCCAAGTAAATATGTGTTTTTAATATTCAACCCTGAAAATTAGTAATTC
        790             810             830
AGATGATAAAAGCTCATGTTTTGGTGTCTTTGTACTCAGATTGTGAACAGGCATATTTCA
        850             870             890
CTGATTTAGACTTAGTATACTTGATGAGAATGCTCAGGTTGAAGAGATAGTTCTGTCAGC
        910             930             950
AATCCAACATCTATAGCAAATGTGGAAAAAGTAATCAACTCATATTTCACGAATTTGATGT
        970             990             1010
ATGTTGTGATTTAGAGGGCATGAGATAAAGTTTATATTTGAACTGTGTGGGGTAGGGGGA
        1030            1050            1070
AGAAGAGGTTGCTTAAGCAAATGGGGGTGATTGAGGAACAAGATGTCTCTAAGATGAG
        1090            1110            1130
AAGTTATTTCTTGCATCATAGAAGCACTCTCCACCCGGGAGTGATTGTGTTAACTAT
        1150            1170            1190
AAATCATTTATATCTGTACATTAAAGCAGATTCCCTCAATTAGGCAAATTTGGTTAGCCA
```

FIG. 1C

```
         1210                1230                1250
AGCCCAAGTTATTGTTTGTACTTGAAAGTAATAAAGCTGCATTTCCTTAAAAATATATTC
         1270                1290                1310
TGTAGTTAAGACTTTGTCTTGCTTCCGGAATTCCTGTTTTTCTTTCCTCTAGAGACCT
         1330                1350                1370
CGGCTTGCAACTGGATCAAACGCTGTCGAAAGGATGTAATAGGCAGAGCAACTGTTACC
         1390                1410                1430
AAGAAGGCCACCACCCCCACCCAAAGGCAGTGAGGAGTGTGGGGCTTCGTCTGGGCTCCC
         1450                1470                1490
CCGAGTCTCAACAGTAATCAACAGTCAGTGTTGATTGCAACTTTTCAAGGTCAGCCACC
         1510                1530                1550
GGGAGTAGCCTATTCCCTCTAGGAACCTTGGAGGGCATACCCTTGCTGGGACTCAACTTGG
         1570                1590                1610
CTGAGAAATGCACAAGATGCCAAAGGAGGAAGGATTATAGGGGCGTGTGTGTGACCCCC
         1630                1650                1670
AAGACCGATCTTCCGCTATCACCCTAATCTCCGGTTCCCCGTACCCGGGGCGGGGTGAG
         1690                1710                1730
TATGTGACATGTGCCTAACTCTCAGCAACTTCGGCAGCAGGTGTCGATCCTAACTAA
         1750                1770                1790
GCAGGAGCTGCGGCTGCGGGTGTGCCCTCACCAAGCCATGCGAGCCCGGCGGCGCTTC
```

FIG. 1D

```
            .         M  R  A  P  G  A  L  L
TCGCCCGCATGTCGCGGGCTACTGCTTCTGCTTCAAGGTGTCTGCCTCTTCTGCCC
1810          1830            1850
 A  R  M  S  R  L  L  L  L  L  K  V  S  A  S  S  A  L
                  1870                    1890              1910
            .                   .                   .
TCGGGGTCGCCCCTGCCTCGTCCAGAAACGAATGTCTGGGGAGAGTCTGCACCTACAG
 G  V  A  P  A  S  R  N  E  T  C  L  G  E  S  C  A  P  T  V
       1930                    1950                    1970
            .                   .                   .
TGATCCAGCGCCGGCGCGGGCGACGCCTGGGACCGGGAAATTCTGCAAGAGACGTTCTGC
 I  Q  R  R  R  G  R  D  A  W  G  P  G  N  S  A  R  D  V  L  R
             1990                    2010                    2030
            .                   .                   .
GAGCCCGAGCACCCAGGAGGAGCAGGGGCAGCGTTCTTGCGGACCCTCCTGGGACC
 A  R  P  R  E  E  Q  G  A  A  F  L  A  G  P  S  W  D  L
       2050                    2070                    2090
            .                   .                   .
TGCCCGGCGGCCCCGGACCCGTGACCCGGCTGCAGGCAGAGAGGGCGGAGGCGTGACAGCCG
 A  P  D  R  D  P  A  A  G  R  G  A  E  A  S  T  A  G
       2110                    2130                    2150
            .                   .                   .
GACCCCCGGGACCTCCAACCAGGCCCACCTGTCCCCTGGAGGTGGAAAGGTGCTCGGGGTC
 P  P  G  P  P  T  R  P  P  V  P  W  R  W  K  G  A  R  G  Q
       2170                    2190                    2210
            .                   .                   .
AGGAGCCTTCTGAAACTTTGGGGAGAGGGAACCCCACGGCCCTCTTCCTTCAGA
 E  P  S  E  T  L  G  R  G  N  P  T  A  L  Q  L  F  L  Q  I
       2230                    2250                    2270
```

FIG. 1E

```
TCTCAGAGGAGGAAGAGAAGGGTCCCAGAGGCGCTGTCATTTCCGGGCGTAGCCAGGAGC
 S  E  E  E  E  K  G  P  R  G  A  V  I  S  G  R  S  Q  E  Q
                    2290                     2310            2330

AGAGTGTGAAGACAGTCCCCGGAGCCAGCGATCTTTTTACTGTCCAAGGAGAGCCGGGA
 S  V  K  T  V  P  G  A  S  D  L  F  Y  C  P  R  R  A  G  K
              2350                     2370                     2390

AACTCCAGGGTTCCCACCACAAGCCCCTGTCCAAGACGGCCAATGACTGGCGGGCACG
 L  Q  G  S  H  H  K  P  L  S  K  T  A  N  G  L  A  G  H  E
        2410                     2430                     2450

AAGGGTGGACAATTGCACTCCCGGGCCGCTGGCCCAGAATGGATCCTTGGGTGAAG
 G  W  T  I  A  L  P  G  R  A  L  A  Q  N  G  S  L  G  E  G
        2470                     2490                     2510

GAATCCATGATCCTGGGGGTCCCCGCCGGGAAACAGCACGAACCGGCTGTGAGACTGA
 I  H  D  P  G  G  P  R  R  G  N  S  T  N  R  R  V  R  L  K
              2530                     2550                     2570

AGAACCCCTTCTACCCGCTGACCCAGGAGTCCTATGGAGCCTACGCGGTCATGTGTCTGT
 N  P  F  Y  P  L  T  Q  E  S  Y  G  A  Y  A  V  M  C  L  S
              2590                     2610                     2630

CCGTGGTGATCTTCGGGACCGGCATCATTGGCAACCTGGCTGTGATGTGCATCGTGTGCC
 V  V  I  F  G  T  G  I  I  G  N  L  A  V  M  C  I  V  C  H
              2650                     2670                     2690

ACAACTACTACATGCGGAGCATCTCCAACTCCCTCTTGGCCAACCTGGTCTTCTGGGACT
```

FIG. 1F

```
                  N Y Y M R S I S N S L L A N L V F W D F
                    2710                 2730                 2750
TTCTCATCATCTTCTTCTGCCTTCCGCTGGTCATCTTCCACGAGCTGACCAAGAAGTGGC
 L I F F C L P L V I F H E L T K K W L
          2770                 2790                 2810
TGGTGGAGGACTTCTCCTGCAAGATCGTGCCCTATATAGAGGTCGCTTCTCTGGGAGTCA
 V E D F S C K I V P Y I E V A S L G V T
          2830                 2850                 2870
CCACTTTCACCTTATGTGCTCTGTGCATAGACCGCTTCCGTGCTGCCACCAACGTACAGA
 T F T L C A L C I D R F R A A T N V Q M
          2890                 2910                 2930
TGTACTACGAAATGATCGAAAACTGTTCCTCAACAACTGCCAAACTTGCTGTTATATGGG
 Y Y E M I E N C S S T T A K L A V I W V
          2950                 2970                 2990
TGGGAGCTCTATTGTTAGCACTTCCAGAAGTTGTCTCCGCCAGCTGAGCAAGGAGGATT
 G A L L L A L P E V V L R Q L S K E D L
          3010                 3030                 3050
TGGGGTTTAGTGGCCGAGCTCCGGCAGAAAGGTGCATTATTAAGATCTCTCCTGATTTAC
 G F S G R A P A E R C I I K I S P D L P
          3070                 3090                 3110
CAGACACCATCTATGTTCTAGCCCTCACCTACGACAGTGCGAGACTGTGGTGGTATTTTG
 D T I Y V L A L T Y D S A R L W W Y F G
          3130                 3150                 3170
```

FIG. 1G

```
GCTGTTACTTTTGTTGCCCACGCTTTCACCATCACCTGCTCTCTAGTGACTGCGAGGA
 C  Y  F  C  L  P  T  L  F  T  I  T  C  S  L  V  T  A  R  K
    3190                      3210                      3230

AAATCCGCAAAGCAGAGAAAGCCTGTACCCGAGGGAATAAACGGCAGATTCAACTAGAGA
 I  R  K  A  E  K  A  C  T  R  G  N  K  R  Q  I  Q  L  E  S
    3250                      3270                      3290

GTCAGATGAACTGTACAGTGGCACTGACCATTTTATATGGATTGGGCATTATTCCTG
 Q  M  N  C  T  V  V  A  L  T  I  L  Y  G  L  G  I  I  P  E
    3310                      3330                      3350

AAAATATCTGCAACATTGTACTGCCTACATGGCTACACAGGGGTTCACAGCAGACAATGG
 N  I  C  N  I  V  T  A  Y  M  A  T  G  V  S  Q  Q  T  M  D
    3370                      3390                      3410

ACCTCCTTAAATATCATCAGCCAGTTCCTTTTGTTCTTTAAGTCCTGTGTCACCCCAGTCC
 L  L  N  I  I  S  Q  F  L  L  F  F  K  S  C  V  T  P  V  L
    3430                      3450                      3470

TCCTTTCTGTCTCTGCAAACCCTTCAGTCGGCCCTTCATGGAGTGCTGCTGTTGCT
 L  F  C  L  C  K  P  F  S  R  A  F  M  E  C  C  C  C  C
    3490                      3510                      3530

GTGAGGAATGCATTCAGAAGTCTTCAACGGTGACCAGTGATGACAATGACAACGAGTACA
 E  E  C  I  Q  K  S  S  T  V  T  S  D  D  N  D  N  E  Y  T
    3550                      3570                      3590

CCACGGAACTCGAACTCTCGCCTTTCAGTGCCATACGCCGTGAAATGTCCACTTTTGCTT
```

FIG. 1H

```
T  E  L  E  L  S  P  F  S  A  I  R  R  E  M  S  T  F  A  S
      3610            3630                  3650
CTGTCGGAACTCATTGCTGAAGGACAGTACTTGGTTGGGTCAGATTTATTTGTTTGATTT
V  G  T  H  C  *
      3670            3690                  3710
TCATATCCCGTGAAAGTTTTAATTCATATTTTCCTTATAGGGAAAAATGCAAAAAGA
      3730                  3750                  3770
AACAATAAAGAAAGAAATATTAACTACTGTAGAACTGATTTTACAAATTAATATTGTGC
      3790                  3810                  3830
TTTGAAAAAGTTTCTATTTAGTTATTTAAGAAGAATGAGAAGGCCAATAGTTTTAGAT
      3850                  3870                  3890
TATTTTATCTGGTATGGTGCTAATATATTTATTTGAAAAAAGTTACTGCAACTTAACTTAA
      3910                  3930                  3950
AATTGCTAACGTTTTTTCTTTCTTTTAAAATACAATTATTGTATATTAATTATAGCAATG
      3970                  3990                  4010
TGATTTTGTAGGTTATTTTATATTTGAGTTGTGATTGAAAGTATGTTGTATATGGTATTG
      4030                  4050                  4070
TGAGATGATTTGTACTTGGAAGCATTCACAAAGTAGCACCAAATAAATTACACTTTATTC
      4090                  4110                  4130
TTTAATGTCATTGTCAATCTTACTTTTAACCAATATTCAATAAATCTTCTAATTGCCTTAA
      4150
AAAAAAAAAAAAAA
```

FIG. 3A1

|   | | | | | | | | | | | | | | | | | |
|---|---|---|---|---|---|---|---|---|---|---|---|---|---|---|---|---|---|
| | M | A | P | - | - | - | L | - | - | R | A | S | - | - | L | A | L | - |
| | | | | | | | | | 10 | | | | | | | | | |
| 1 | M | R | A | P | G | A | L | L | A | R | M | S | R | L | L | L | L | L |
| 1 | M | E | - | - | - | T | L | C | L | R | A | S | F | W | L | A | L | V |
| 1 | M | Q | P | P | P | S | L | C | G | R | A | L | V | A | L | V | L | - |
| 1 | M | A | T | - | - | - | - | - | - | - | V | I | L | F | V | A | W | M |
| 1 | M | A | L | - | - | - | - | - | - | - | - | - | - | - | - | - | - | - |
| 1 | M | P | P | - | - | - | - | - | - | - | - | - | - | - | - | - | - | - |

|   | | | | | | | | | | | | | | | | | |
|---|---|---|---|---|---|---|---|---|---|---|---|---|---|---|---|---|---|
| | - | - | - | - | - | - | - | - | - | P | - | R | S | X | P | L | L | - | - |
| | | | | | | | | | 60 | | | | | | | | | |
| 51 | R | R | G | R | D | A | W | G | P | G | N | S | A | R | D | V | L | R |
| 22 | - | - | - | - | - | - | - | - | N | P | E | R | Y | S | T | N | L | - |
| 26 | G | E | E | R | G | - | F | P | P | D | R | A | T | P | L | L | - | - |
| 20 | Y | Q | E | - | - | - | F | Q | T | Q | Q | N | F | P | D | I | - | - |
| 4 | - | - | - | - | - | - | - | - | - | - | N | D | C | F | L | L | - | - |
| 4 | - | - | - | - | - | - | - | - | - | - | R | R | L | P | N | L | - | - |

|   | | | | | | | | | | | | | | | | | |
|---|---|---|---|---|---|---|---|---|---|---|---|---|---|---|---|---|---|
| | - | - | - | - | - | - | - | - | - | - | - | - | - | - | - | - | - | - |
| | | | | | | | | | 110 | | | | | | | | | |
| 101 | G | A | E | A | S | T | A | G | P | P | G | P | P | T | R | P | P | V |
| 47 | - | - | - | - | - | - | - | - | - | - | - | - | - | - | - | - | - | - |
| 61 | - | - | - | - | - | - | - | - | - | - | - | - | - | - | - | - | - | - |
| 53 | - | - | - | - | - | - | - | - | - | - | - | - | - | - | - | - | - | - |
| 28 | - | - | - | - | - | - | - | - | - | - | - | - | - | - | - | - | - | - |
| 29 | - | - | - | - | - | - | - | - | - | - | - | - | - | - | - | - | - | - |

|   | | | | | | | | | | | | | | | | | |
|---|---|---|---|---|---|---|---|---|---|---|---|---|---|---|---|---|---|
| | G | P | T | N | - | P | - | G | - | - | - | - | - | - | P | P | - | - |
| | | | | | | | | | 160 | | | | | | | | | |
| 151 | E | E | E | K | G | P | R | G | A | V | I | S | G | R | S | Q | E | Q |
| 53 | Q | P | T | N | L | V | L | - | - | - | - | - | - | - | P | S | N | G |
| 67 | A | P | A | E | V | P | K | G | D | R | T | A | G | S | P | P | R | T |
| 57 | G | A | L | M | S | T | G | N | V | L | N | M | S | P | P | P | - | |
| 33 | D | W | S | H | - | - | - | - | - | - | - | - | - | - | - | - | - | - |
| 35 | G | T | T | A | - | - | - | - | - | - | - | - | - | - | - | - | - | - |

```
- - - - A C - - S - - -    Majority
         40          50
C L G E S C A P T V I Q    49.pep.4/29
- - - - G C V I S D - -    HumanETA.PEP
- - - - A C G L S R I W    HuETBR.PEP
- - - - A C L M V G V C    FROG.ET3R.PEP
- - - - - - - - - - - -    GRP-R
- - - - - - - - - - - -    NeuroMBR/rat

- X X X S - D - - - - -    Majority
         90         100
P A A P D R D P A A G R    49.pep.4/29
- - - - - - S - - - - -    HumanETA.PEP
W P K G S N A - - - - -    HuETBR.PEP
V Q L D S - - - - - - -    FROG.ET3R.PEP
- H S A D - - - - - - -    GRP-R
- E V W E N D - - - - -    NeuroMBR/rat

- - - - - - F L P X S D    Majority
        140         150
P T A L Q L F L Q I S E    49.pep.4/29
- - - - - - F L V T T H    HumanETA.PEP
- - - - - - S L A R S L    HuETBR.PEP
- - - - - - - - I Q N N    FROG.ET3R.PEP
- - - - - - - L P V N D    GRP-R
- - - - - - F L P D S D    NeuroMBR/rat

- - - - - - - - - - - -    Majority
        190         200
L Q G S H H K P L S K T    49.pep.4/29
- - - - - - - - - - - -    HumanETA.PEP
- - - - - - - - - - - -    HuETBR.PEP
- - - - - - - - - - - -    FROG.ET3R.PEP
- - - - - - - - - - - -    GRP-R
- - - - - - - - - - - -    NeuroMBR/rat
```

```
- - - - - - - - K I K X A  Majority
        240            250
N S T N R R V R L K N P  49.pep.4/29
- - - - - - - T K I T S A  HumanETA.PEP
- - - - - - - I E I K E T  HuETBR.PEP
- - - - - - - A K I R H A  FROG.ET3R.PEP
- - - - - - - - - - P G I  GRP-R
- - - - - - - - - - E L V  NeuroMBR/rat N K Y M R N G P N I L I  Majority
        290            300
N Y Y M R S I S N S L L  49.pep.4/29
N K Y M R N G P N A L I  HumanETA.PEP
N K C M R N G P N I L I  HuETBR.PEP
N K C M R N G P N V L I  FROG.ET3R.PEP
V K S M R N V P N L F I  GRP-R
N S T M R S V P N I F I  NeuroMBR/rat G C K L V P F I Q L A S  Majority
        340            350
- C K I V P Y I E V A S  49.pep.4/29
L C K L F P F L Q K S S  HumanETA.PEP
M C K L V P F I Q K A S  HuETBR.PEP
- - - I Y Q L V H L Y R  FROG.ET3R.PEP
G C K L I P F I Q L T S  GRP-R
G C K L I P A I Q L T S  NeuroMBR/rat A V L I W V V S V L L A  Majority
        390            400
L A V I W V G A L L L A  49.pep.4/29
I V S I W I L S F I L A  HumanETA.PEP
I V L I W V V S V V L A  HuETBR.PEP
L T L I W A V A I I V A  FROG.ET3R.PEP
A A F I W I I S M L L A  GRP-R
A V G I W V V S V L L A  NeuroMBR/rat
```

```
- - - - - Y Q K A K S W   Majority
          440       450

V L A L T Y D S A R L W   49.pep.4/29
- - - - - Y Q D V K D W   HumanETA.PEP
- - - - - Y K T A K D W   HuETBR.PEP
- - - - - Y Q E V K V W   FROG.ET3R.PEP
- - - - - H P K I H S M   GRP-R
- - - - - H P K I H S V   NeuroMBR/rat N D H L K Q Q - - - R R   Majority
      490         500

T R G N K R Q I Q L E S   49.pep.4/29
S E H L K Q - - - - R R   HumanETA.PEP
N D H L K Q - - - - R R   HuETBR.PEP
N D H M K Q - - - - R R   FROG.ET3R.PEP
N I H V K K Q I E S R K   GRP-R
N E H T K K Q M E T R K   NeuroMBR/rat

- - - - R S C E L - E I   Majority
         540        550

- - - - - - - - - - - M   49.pep.4/29
- M D K N R C E L - - -   HumanETA.PEP
- N D P N R C E L - - -   HuETBR.PEP
L K N K R S C I M A E I   FROG.ET3R.PEP
- - - - R S Y H Y S E V   GRP-R
- - - - R S F N Y K E I   NeuroMBR/rat K N C F N S C L C C C C   Majority
       590        600

S R A F M E C C C C C C   49.pep.4/29
K N C F Q S C L C C C C   HumanETA.PEP
K N C F K S C L C C W C   HuETBR.PEP
K N C F Q S C L C C W C   FROG.ET3R.PEP
R K Q F N T Q L L C C Q   GRP-R
R K H F N S Q L C C G Q   NeuroMBR/rat
```

Decoration 'Decoration #1': Shaded with solid residues that match the Consensus exactly.

```
     G T S L K S K A N D V X T D S - L N S G
         |                 |
        620               630
     E Y T T E L E L S P F S A I R R E M S T
     G T S I Q W K N H D Q N N H - - - N T D
     Q S C L K F K A N D H G Y D - - - N F -
     G S G G K W K A N G H D L D L D R S S S
     M T S L K S T N P S V A T F S - L I N G
     M T S L K S N A K N V V T N S V L L N G
```

```
     R S S N K E S S S          Majority
         |
        640
     F A S V G T H C            49.pep.4/29
     R S S H K D S M N          HumanETA.PEP
     R S S N K Y S S S          HuETBR.PEP
     R L S N K Y S S S          FROG.ET3R.PEP
     N I C - H E R Y V          GRP-R
     H S T K Q E I A L          NeuroMBR/rat
```

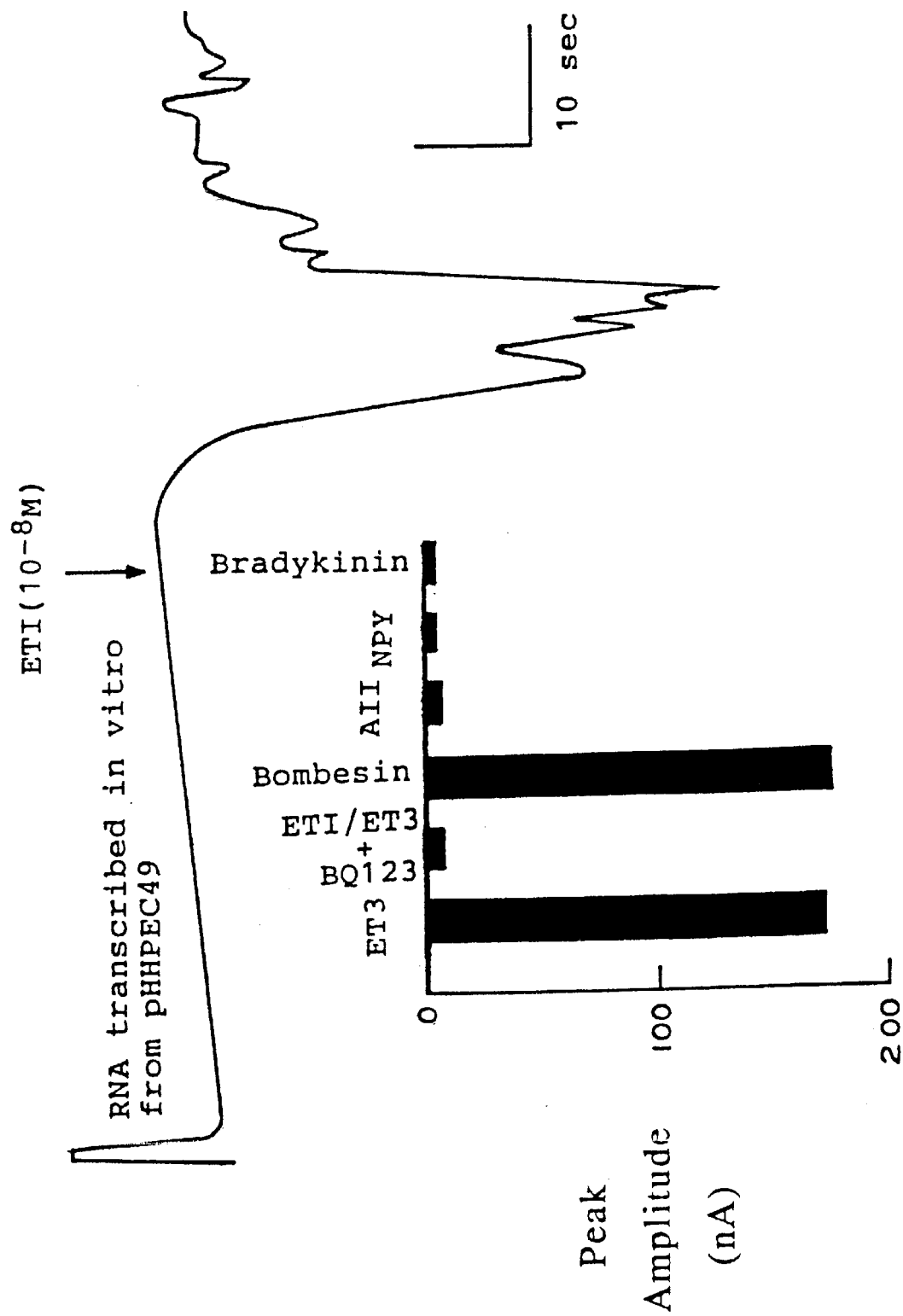

SEQUENCE LISTING

<160> NUMBER OF SEQ ID NOS: 13

<210> SEQ ID NO 1
<211> LENGTH: 4156
<212> TYPE: DNA
<213> ORGANISM: Human
<220> FEATURE:
<221> NAME/KEY: CDS
<222> LOCATION: (1779)..(3620)
<223> OTHER INFORMATION:

<400> SEQUENCE: 1

| | | | | | |
|---|---|---|---|---|---|
| cccactatgt | tggccaggat | ggtcttgatt | tcttgacctc | gtgttctgcc | cgcctctacc | 60 |
| tcccaaagtg | ccgggattac | aggcgtgact | gctgtgcccg | gccccagcat | cactttata | 120 |
| gctttctgtg | cctcttcctc | tgggccttgg | tgtatgaagc | cacttgcctt | tctctgttgg | 180 |
| gaagcgagca | gaatcagatt | gctactcatg | atgcagtccg | ggcagggcat | actgtcacct | 240 |
| ttggctgtgg | acacagttgt | caggataggg | gagaagccct | ttaggtccgt | cttcttgaca | 300 |
| cagccctcct | acctggttac | gctggtgctt | tcgcttggtt | tagacaacca | agacacttga | 360 |
| gaattatgct | gtcctcagaa | tgtctgatga | aagaacaga | ttcactttt | ggacacaatg | 420 |
| cccattagcc | atctttggca | gtgtttctga | tcaaaggttc | cccatgcctg | ctctaggaaa | 480 |
| gtaaactttt | ttcagaataa | atcctcaaat | ggattactga | gtagtctttg | caccattccc | 540 |
| atcagcctaa | tcagactgaa | tggtcacgct | cagtgcaaaa | agctgttttg | ctgttaggat | 600 |
| gtttcagtgt | ttcttgtctt | tcctggaaca | gttcagttgt | ttaaatttag | taattcaatc | 660 |
| ctgaccagtg | taaacccact | taattattgc | agcctaaaga | attcagctac | ttctactctt | 720 |
| cataaatgtg | cccaagtaaa | tatgtgtttt | taatattcaa | ccctggaaaa | ttagtaattc | 780 |
| agatgataaa | agctcatgtt | ttggtgtctt | tgtactcaga | ttgtgaacag | gcatatttca | 840 |
| ctgatttaga | cttagtatac | ttgatgagaa | tgctcaggtt | gaagagatag | ttctgtcagc | 900 |
| aatccaacat | ctatagcaat | gtggaaaaag | taatcaactc | atatttcacg | aatttgatgt | 960 |
| atgttgtgat | ttagagggca | tgagataaag | tttatatttg | aactgtgtgg | ggtaggggga | 1020 |
| agaagaggtt | gcttaagcaa | atgggggggt | gattgaggaa | caagatgtct | ctaagatgag | 1080 |
| aagttatttt | cttgcatcat | agaagcactc | tctccacccg | ggagtgattg | tgttaactat | 1140 |
| aaatcattta | tatctgtaca | ttaaagcaga | ttccctcaat | taggcaaatt | tggttagcca | 1200 |
| agcccaagtt | attgtttgta | cttgaaagta | ataaagctgc | atttccttaa | aaatatattc | 1260 |
| tgtagttaag | actttgtctt | gctttccgga | attcctgttt | ttcttttcct | ctagagacct | 1320 |
| cggcttgcaa | ctggatcaaa | cgctgtcgaa | aggatgtaaa | taggcagagc | aactgttacc | 1380 |
| aagaaggcca | ccaccccac | ccaaaggcag | tgaggagtgt | ggggcttcgt | ctgggctccc | 1440 |
| ccgagtctca | acagtaatca | acagtcaggt | gttgattgca | acttttcaag | gtcagccacc | 1500 |
| gggagtagcc | tattccctct | aggaaccttg | gagggcatac | cttgctggga | ctcaacttgg | 1560 |
| ctgagaaatg | cacaagatgc | caaggagga | aggattatag | ggggcgtgtg | tgtgaccccc | 1620 |
| aagaccgatc | ttccgctatc | accctaatct | ccggttcccc | gctacccggg | cggggtgag | 1680 |
| tatgtgacat | gtgcctaact | ctcagcagca | acttcggcag | caggtgtcga | tcctaactaa | 1740 |
| gcaggagctg | cggctgccgg | gtgtgccctc | accaagcc atg cga gcc ccg ggc gcg | | 1796 |
| | | | Met Arg Ala Pro Gly Ala | | |
| | | | 1       5 | | |
| ctt ctc gcc cgc atg tcg cgg cta ctg ctt ctg cta ctg ctc aag gtg | | | | | | 1844 |

-continued

```
Leu Leu Ala Arg Met Ser Arg Leu Leu Leu Leu Leu Leu Lys Val
         10                  15                  20 tct gcc tct tct gcc ctc ggg gtc gcc cct gcg tcc aga aac gaa act      1892
Ser Ala Ser Ser Ala Leu Gly Val Ala Pro Ala Ser Arg Asn Glu Thr
         25                  30                  35 tgt ctg ggg gag agc tgt gca cct aca gtg atc cag cgc cgc ggc agg      1940
Cys Leu Gly Glu Ser Cys Ala Pro Thr Val Ile Gln Arg Arg Gly Arg
 40                  45                  50 gac gcc tgg gga ccg gga aat tct gca aga gac gtt ctg cga gcc cga      1988
Asp Ala Trp Gly Pro Gly Asn Ser Ala Arg Asp Val Leu Arg Ala Arg
 55                  60                  65                  70 gca ccc agg gag gag cag ggg gca gcg ttt ctt gcg gga ccc tcc tgg      2036
Ala Pro Arg Glu Glu Gln Gly Ala Ala Phe Leu Ala Gly Pro Ser Trp
                 75                  80                  85 gac ctg ccg gcg gcc ccg gac cgt gac ccg gct gca ggc aga ggg gcg      2084
Asp Leu Pro Ala Ala Pro Asp Arg Asp Pro Ala Ala Gly Arg Gly Ala
             90                  95                 100 gag gcg tcg aca gcc gga ccc ccg gga cct cca acc agg cca cct gtc      2132
Glu Ala Ser Thr Ala Gly Pro Pro Gly Pro Pro Thr Arg Pro Pro Val
         105                 110                 115 ccc tgg agg tgg aaa ggt gct cgg ggt cag gag cct tct gaa act ttg      2180
Pro Trp Arg Trp Lys Gly Ala Arg Gly Gln Glu Pro Ser Glu Thr Leu
     120                 125                 130 ggg aga ggg aac ccc acg gcc ctc cag ctc ttc ctt cag atc tca gag      2228
Gly Arg Gly Asn Pro Thr Ala Leu Gln Leu Phe Leu Gln Ile Ser Glu
135                 140                 145                 150 gag gaa gag aag ggt ccc aga ggc gct gtc att tcc ggg cgt agc cag      2276
Glu Glu Glu Lys Gly Pro Arg Gly Ala Val Ile Ser Gly Arg Ser Gln
                 155                 160                 165 gag cag agt gtg aag aca gtc ccc gga gcc agc gat ctt ttt tac tgt      2324
Glu Gln Ser Val Lys Thr Val Pro Gly Ala Ser Asp Leu Phe Tyr Cys
             170                 175                 180 cca agg aga gcc ggg aaa ctc cag ggt tcc cac cac aag ccc ctg tcc      2372
Pro Arg Arg Ala Gly Lys Leu Gln Gly Ser His His Lys Pro Leu Ser
         185                 190                 195 aag acg gcc aat gga ctg gcg ggg cac gaa ggg tgg aca att gca ctc      2420
Lys Thr Ala Asn Gly Leu Ala Gly His Glu Gly Trp Thr Ile Ala Leu
     200                 205                 210 ccg ggc cgg gcg ctg gcc cag aat gga tcc ttg ggt gaa gga atc cat      2468
Pro Gly Arg Ala Leu Ala Gln Asn Gly Ser Leu Gly Glu Gly Ile His
215                 220                 225                 230 gat cct ggg ggt ccc cgc cgg gga aac agc acg aac cgg cgt gtg aga      2516
Asp Pro Gly Gly Pro Arg Arg Gly Asn Ser Thr Asn Arg Arg Val Arg
                 235                 240                 245 ctg aag aac ccc ttc tac ccg ctg acc cag gag tcc tat gga gcc tac      2564
Leu Lys Asn Pro Phe Tyr Pro Leu Thr Gln Glu Ser Tyr Gly Ala Tyr
             250                 255                 260 gcg gtc atg tgt ctg tcc gtg gtg atc ttc ggg acc ggc atc att ggc      2612
Ala Val Met Cys Leu Ser Val Val Ile Phe Gly Thr Gly Ile Ile Gly
         265                 270                 275 aac ctg gcg gtg atg tgc atc gtg tgc cac aac tac tac atg cgg agc      2660
Asn Leu Ala Val Met Cys Ile Val Cys His Asn Tyr Tyr Met Arg Ser
     280                 285                 290 atc tcc aac tcc ctc ttg gcc aac ctg gtc ttc tgg gac ttt ctc atc      2708
Ile Ser Asn Ser Leu Leu Ala Asn Leu Val Phe Trp Asp Phe Leu Ile
295                 300                 305                 310 atc ttc ttc tgc ctt ccg ctg gtc atc ttc cac gag ctg acc aag aag      2756
Ile Phe Phe Cys Leu Pro Leu Val Ile Phe His Glu Leu Thr Lys Lys
                 315                 320                 325
```

```
                                                               -continued tgg ctg gtg gag gac ttc tcc tgc aag atc gtg ccc tat ata gag gtc    2804
Trp Leu Val Glu Asp Phe Ser Cys Lys Ile Val Pro Tyr Ile Glu Val
            330                 335                 340 gct tct ctg gga gtc acc act ttc acc tta tgt gct ctg tgc ata gac    2852
Ala Ser Leu Gly Val Thr Thr Phe Thr Leu Cys Ala Leu Cys Ile Asp
345                 350                 355 cgc ttc cgt gct gcc acc aac gta cag atg tac tac gaa atg atc gaa    2900
Arg Phe Arg Ala Ala Thr Asn Val Gln Met Tyr Tyr Glu Met Ile Glu
        360                 365                 370 aac tgt tcc tca aca act gcc aaa ctt gct gtt ata tgg gtg gga gct    2948
Asn Cys Ser Ser Thr Thr Ala Lys Leu Ala Val Ile Trp Val Gly Ala
375                 380                 385                 390 cta ttg tta gca ctt cca gaa gtt gtt ctc cgc cag ctg agc aag gag    2996
Leu Leu Leu Ala Leu Pro Glu Val Val Leu Arg Gln Leu Ser Lys Glu
                395                 400                 405 gat ttg ggg ttt agt ggc cga gct ccg gca gaa agg tgc att att aag    3044
Asp Leu Gly Phe Ser Gly Arg Ala Pro Ala Glu Arg Cys Ile Ile Lys
            410                 415                 420 atc tct cct gat tta cca gac acc atc tat gtt cta gcc ctc acc tac    3092
Ile Ser Pro Asp Leu Pro Asp Thr Ile Tyr Val Leu Ala Leu Thr Tyr
        425                 430                 435 gac agt gcg aga ctg tgg tgg tat ttt ggc tgt tac ttt tgt ttg ccc    3140
Asp Ser Ala Arg Leu Trp Trp Tyr Phe Gly Cys Tyr Phe Cys Leu Pro
440                 445                 450 acg ctt ttc acc atc acc tgc tct cta gtg act gcg agg aaa atc cgc    3188
Thr Leu Phe Thr Ile Thr Cys Ser Leu Val Thr Ala Arg Lys Ile Arg
455                 460                 465                 470 aaa gca gag aaa gcc tgt acc cga ggg aat aaa cgg cag att caa cta    3236
Lys Ala Glu Lys Ala Cys Thr Arg Gly Asn Lys Arg Gln Ile Gln Leu
                475                 480                 485 gag agt cag atg aac tgt aca gta gtg gca ctg acc att tta tat gga    3284
Glu Ser Gln Met Asn Cys Thr Val Val Ala Leu Thr Ile Leu Tyr Gly
            490                 495                 500 ttg ggc att att cct gaa aat atc tgc aac att gtt act gcc tac atg    3332
Leu Gly Ile Ile Pro Glu Asn Ile Cys Asn Ile Val Thr Ala Tyr Met
        505                 510                 515 gct aca ggg gtt tca cag cag aca atg gac ctc ctt aat atc atc agc    3380
Ala Thr Gly Val Ser Gln Gln Thr Met Asp Leu Leu Asn Ile Ile Ser
520                 525                 530 cag ttc ctt ttg ttc ttt aag tcc tgt gtc acc cca gtc ctc ctt ttc    3428
Gln Phe Leu Leu Phe Phe Lys Ser Cys Val Thr Pro Val Leu Leu Phe
535                 540                 545                 550 tgt ctc tgc aaa ccc ttc agt cgg gcc ttc atg gag tgc tgc tgt tgt    3476
Cys Leu Cys Lys Pro Phe Ser Arg Ala Phe Met Glu Cys Cys Cys Cys
                555                 560                 565 tgc tgt gag gaa tgc att cag aag tct tca acg gtg acc agt gat gac    3524
Cys Cys Glu Glu Cys Ile Gln Lys Ser Ser Thr Val Thr Ser Asp Asp
            570                 575                 580 aat gac aac gag tac acc acg gaa ctc gaa ctc tcg cct ttc agt gcc    3572
Asn Asp Asn Glu Tyr Thr Thr Glu Leu Glu Leu Ser Pro Phe Ser Ala
        585                 590                 595 ata cgc cgt gaa atg tcc act ttt gct tct gtc gga act cat tgc tga    3620
Ile Arg Arg Glu Met Ser Thr Phe Ala Ser Val Gly Thr His Cys
600                 605                 610 aggacagtac ttggttgggt cagatttatt tgtttgattt tcatatcccg tgaaagtttt   3680
taattcatat ttttcccttat agggaaaaat gcaaaaaaga aacaataaag aaagaaatat   3740
taactactgt agaactgatt ttacaaatta atatttgtgc tttgaaaaaa agtttctatt   3800
tagttattta agaagaatga gaaggccaat agttttagat tatttttatct ggtatggtgc   3860
```

-continued

```
taatatttta tttgaaaaaa gttactgcaa cttaacttaa aattgctaac gttttttctt    3920
cttttaaaaa tacaattatt gtatattaat tatagcaatg tgattttgta ggttatttta    3980
tatttgagtt gtgattgaaa gtatgttgta tatggtattg tgagatgatt tgtacttgga    4040
agcattcaca aagtagcacc aaataaatta cactttattc tttaatgtca ttgtcaatct    4100
acttttaacc aatattcaat aaatcttcta attgccttaa aaaaaaaaaa aaaaaa       4156
```

<210> SEQ ID NO 2
<211> LENGTH: 613
<212> TYPE: PRT
<213> ORGANISM: Human

<400> SEQUENCE: 2

```
Met Arg Ala Pro Gly Ala Leu Leu Ala Arg Met Ser Arg Leu Leu Leu
1               5                   10                  15

Leu Leu Leu Lys Val Ser Ala Ser Ser Ala Leu Gly Val Ala Pro
            20                  25                  30

Ala Ser Arg Asn Glu Thr Cys Leu Gly Glu Ser Cys Ala Pro Thr Val
        35                  40                  45

Ile Gln Arg Arg Gly Arg Asp Ala Trp Gly Pro Gly Asn Ser Ala Arg
50                  55                  60

Asp Val Leu Arg Ala Arg Ala Pro Arg Glu Glu Gln Gly Ala Ala Phe
65                  70                  75                  80

Leu Ala Gly Pro Ser Trp Asp Leu Pro Ala Ala Pro Asp Arg Asp Pro
                85                  90                  95

Ala Ala Gly Arg Gly Ala Glu Ala Ser Thr Ala Gly Pro Pro Gly Pro
            100                 105                 110

Pro Thr Arg Pro Pro Val Pro Trp Arg Trp Lys Gly Ala Arg Gly Gln
        115                 120                 125

Glu Pro Ser Glu Thr Leu Gly Arg Gly Asn Pro Thr Ala Leu Gln Leu
130                 135                 140

Phe Leu Gln Ile Ser Glu Glu Glu Lys Gly Pro Arg Gly Ala Val
145                 150                 155                 160

Ile Ser Gly Arg Ser Gln Glu Gln Ser Val Lys Thr Val Pro Gly Ala
                165                 170                 175

Ser Asp Leu Phe Tyr Cys Pro Arg Arg Ala Gly Lys Leu Gln Gly Ser
            180                 185                 190

His His Lys Pro Leu Ser Lys Thr Ala Asn Gly Leu Ala Gly His Glu
        195                 200                 205

Gly Trp Thr Ile Ala Leu Pro Gly Arg Ala Leu Ala Gln Asn Gly Ser
210                 215                 220

Leu Gly Glu Gly Ile His Asp Pro Gly Gly Pro Arg Arg Gly Asn Ser
225                 230                 235                 240

Thr Asn Arg Arg Val Arg Leu Lys Asn Pro Phe Tyr Pro Leu Thr Gln
                245                 250                 255

Glu Ser Tyr Gly Ala Tyr Ala Val Met Cys Leu Ser Val Ile Phe
            260                 265                 270

Gly Thr Gly Ile Ile Gly Asn Leu Ala Val Met Cys Ile Val Cys His
        275                 280                 285

Asn Tyr Tyr Met Arg Ser Ile Ser Asn Ser Leu Leu Ala Asn Leu Val
        290                 295                 300

Phe Trp Asp Phe Leu Ile Ile Phe Phe Cys Leu Pro Leu Val Ile Phe
305                 310                 315                 320
```

-continued

```
His Glu Leu Thr Lys Lys Trp Leu Val Glu Asp Phe Ser Cys Lys Ile
                325                 330                 335

Val Pro Tyr Ile Glu Val Ala Ser Leu Gly Val Thr Thr Phe Thr Leu
            340                 345                 350

Cys Ala Leu Cys Ile Asp Arg Phe Arg Ala Ala Thr Asn Val Gln Met
        355                 360                 365

Tyr Tyr Glu Met Ile Glu Asn Cys Ser Ser Thr Ala Lys Leu Ala
    370                 375                 380

Val Ile Trp Val Gly Ala Leu Leu Leu Ala Leu Pro Glu Val Val Leu
385                 390                 395                 400

Arg Gln Leu Ser Lys Glu Asp Leu Gly Phe Ser Gly Arg Ala Pro Ala
                405                 410                 415

Glu Arg Cys Ile Ile Lys Ile Ser Pro Asp Leu Pro Asp Thr Ile Tyr
            420                 425                 430

Val Leu Ala Leu Thr Tyr Asp Ser Ala Arg Leu Trp Trp Tyr Phe Gly
        435                 440                 445

Cys Tyr Phe Cys Leu Pro Thr Leu Phe Thr Ile Thr Cys Ser Leu Val
    450                 455                 460

Thr Ala Arg Lys Ile Arg Lys Ala Glu Lys Ala Cys Thr Arg Gly Asn
465                 470                 475                 480

Lys Arg Gln Ile Gln Leu Glu Ser Gln Met Asn Cys Thr Val Val Ala
                485                 490                 495

Leu Thr Ile Leu Tyr Gly Leu Gly Ile Ile Pro Glu Asn Ile Cys Asn
            500                 505                 510

Ile Val Thr Ala Tyr Met Ala Thr Gly Val Ser Gln Gln Thr Met Asp
        515                 520                 525

Leu Leu Asn Ile Ile Ser Gln Phe Leu Leu Phe Phe Lys Ser Cys Val
    530                 535                 540

Thr Pro Val Leu Leu Phe Cys Leu Cys Lys Pro Phe Ser Arg Ala Phe
545                 550                 555                 560

Met Glu Cys Cys Cys Cys Cys Glu Glu Cys Ile Gln Lys Ser Ser
                565                 570                 575

Thr Val Thr Ser Asp Asp Asn Asp Asn Glu Tyr Thr Thr Glu Leu Glu
            580                 585                 590

Leu Ser Pro Phe Ser Ala Ile Arg Arg Glu Met Ser Thr Phe Ala Ser
        595                 600                 605

Val Gly Thr His Cys
    610

<210> SEQ ID NO 3
<211> LENGTH: 29
<212> TYPE: DNA
<213> ORGANISM: Artificial sequence
<220> FEATURE:
<223> OTHER INFORMATION: Primer_Bind

<400> SEQUENCE: 3
cactaagctt aatgcgagcc ccgggcgcg                                    29

<210> SEQ ID NO 4
<211> LENGTH: 32
<212> TYPE: DNA
<213> ORGANISM: Artificial sequence
<220> FEATURE:
<223> OTHER INFORMATION: Primer_Bind

<400> SEQUENCE: 4
```

```
gaacttctag accgtcagca atgagtaccg ac                                    32
```

<210> SEQ ID NO 5
<211> LENGTH: 34
<212> TYPE: DNA
<213> ORGANISM: Artificial sequence
<220> FEATURE:
<223> OTHER INFORMATION: Primer_Bind

<400> SEQUENCE: 5

```
gtccaagctt gccaccatgc gagccccggg cgcg                                  34
```

<210> SEQ ID NO 6
<211> LENGTH: 61
<212> TYPE: DNA
<213> ORGANISM: Artificial sequence
<220> FEATURE:
<223> OTHER INFORMATION: Primer_Bind

<400> SEQUENCE: 6

```
ctagctcgag tcaagcgtag tctgggacgt cgtatgggta gcagcaatga gttccgacag      60
a                                                                      61
```

<210> SEQ ID NO 7
<211> LENGTH: 32
<212> TYPE: DNA
<213> ORGANISM: Artificial sequence
<220> FEATURE:
<223> OTHER INFORMATION: Primer_Bind

<400> SEQUENCE: 7

```
cgggatccgc caccatgcga gccccgggcg cg                                    32
```

<210> SEQ ID NO 8
<211> LENGTH: 29
<212> TYPE: DNA
<213> ORGANISM: Artificial sequence
<220> FEATURE:
<223> OTHER INFORMATION: Primer_Bind

<400> SEQUENCE: 8

```
cgggatcccg ctcagcaatg agttccgac                                        29
```

<210> SEQ ID NO 9
<211> LENGTH: 318
<212> TYPE: PRT
<213> ORGANISM: Human protein

<400> SEQUENCE: 9

```
Met Glu Thr Leu Cys Leu Arg Ala Ser Phe Trp Leu Ala Leu Val Gly
1               5                   10                  15

Cys Val Ile Ser Asp Asn Pro Glu Arg Tyr Ser Thr Asn Leu Ser Asn
                20                  25                  30

His Val Asp Asp Phe Thr Thr Phe Arg Gly Thr Glu Leu Ser Phe Leu
            35                  40                  45

Val Thr Thr His Gln Pro Thr Asn Leu Val Leu Pro Ser Asn Gly Ser
        50                  55                  60

Met His Asn Tyr Cys Pro Gln Gln Thr Lys Ile Thr Ser Ala Phe Lys
65                  70                  75                  80

Tyr Ile Asn Thr Val Ile Ser Cys Thr Ile Phe Ile Val Gly Met Val
                85                  90                  95

Gly Asn Ala Thr Leu Leu Arg Ile Ile Tyr Gln Asn Lys Cys Met Arg
```

-continued

Asn Gly Pro Asn Ala Leu Ile Ala Ser Leu Ala Leu Gly Asp Leu Ile
          115                 120                 125

Tyr Val Val Ile Asp Leu Pro Ile Asn Val Phe Lys Phe Tyr Gln Asp
130                 135                 140

Val Lys Asp Trp Trp Leu Phe Gly Phe Tyr Phe Cys Met Pro Leu Val
145                 150                 155                 160

Cys Thr Ala Ile Phe Tyr Thr Leu Met Thr Cys Glu Met Leu Asn Arg
                165                 170                 175

Arg Asn Gly Ser Leu Arg Ile Ala Leu Ser Glu His Leu Lys Gln Arg
                180                 185                 190

Arg Glu Val Ala Lys Thr Val Phe Cys Leu Val Val Ile Phe Ala Leu
                195                 200                 205

Cys Trp Phe Pro Leu His Leu Ser Arg Ile Leu Lys Lys Thr Val Tyr
210                 215                 220

Asn Glu Met Asp Lys Asn Arg Cys Glu Leu Leu Ser Phe Leu Leu Leu
225                 230                 235                 240

Met Asp Tyr Ile Gly Ile Asn Leu Ala Thr Met Asn Ser Cys Ile Asn
                245                 250                 255

Pro Ile Ala Leu Tyr Phe Val Ser Lys Lys Phe Lys Asn Cys Phe Gln
                260                 265                 270

Ser Cys Leu Cys Cys Cys Cys Tyr Gln Ser Lys Ser Leu Met Thr Ser
                275                 280                 285

Val Pro Met Asn Gly Thr Ser Ile Gln Trp Lys Asn His Asp Gln Asn
                290                 295                 300

Asn His Asn Thr Asp Arg Ser Ser His Lys Asp Ser Met Asn
305                 310                 315

<210> SEQ ID NO 10
<211> LENGTH: 442
<212> TYPE: PRT
<213> ORGANISM: Homo sapiens

<400> SEQUENCE: 10

Met Gln Pro Pro Ser Leu Cys Gly Pro Ala Leu Val Ala Leu Val
1               5                   10                  15

Leu Ala Cys Gly Leu Ser Arg Ile Trp Gly Glu Glu Arg Gly Phe Pro
                20                  25                  30

Pro Asp Arg Ala Thr Pro Leu Leu Gln Thr Ala Glu Ile Met Thr Pro
            35                  40                  45

Pro Thr Lys Thr Leu Trp Pro Lys Gly Ser Asn Ala Ser Leu Ala Arg
        50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
                100                 105                 110

Val Leu Gly Ile Ile Gly Asn Ser Thr Leu Leu Arg Ile Ile Tyr Lys
            115                 120                 125

Asn Lys Cys Met Arg Asn Gly Pro Asn Ile Leu Ile Ala Ser Leu Ala
        130                 135                 140

Leu Gly Asp Leu Leu His Ile Val Ile Asp Ile Pro Ile Asn Val Tyr
145                 150                 155                 160

-continued

```
Lys Leu Leu Ala Glu Asp Trp Pro Phe Gly Ala Glu Met Cys Lys Leu
            165                 170                 175

Val Pro Phe Ile Gln Lys Ala Ser Val Gly Ile Thr Val Leu Ser Leu
            180                 185                 190

Cys Ala Leu Ser Ile Asp Arg Tyr Arg Ala Val Ala Ser Trp Ser Arg
            195                 200                 205

Ile Lys Gly Ile Gly Val Pro Lys Trp Thr Ala Val Glu Ile Val Leu
            210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
            245                 250                 255

Leu His Pro Val Gln Lys Thr Ala Phe Met Gln Phe Tyr Lys Thr Ala
            260                 265                 270

Lys Asp Trp Trp Leu Phe Ser Phe Tyr Phe Cys Leu Pro Leu Ala Ile
            275                 280                 285

Thr Ala Phe Phe Tyr Thr Leu Met Thr Cys Glu Met Leu Arg Lys Lys
            290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
            325                 330                 335

Leu Pro Leu His Leu Ser Arg Ile Leu Lys Leu Thr Leu Tyr Asn Gln
            340                 345                 350

Asn Asp Pro Asn Arg Cys Glu Leu Leu Ser Phe Leu Leu Val Leu Asp
            355                 360                 365

Tyr Ile Gly Ile Asn Met Ala Ser Leu Asn Ser Cys Ile Asn Pro Ile
            370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
            405                 410                 415

Lys Gln Ser Cys Leu Lys Phe Lys Ala Asn Asp His Gly Tyr Asp Asn
            420                 425                 430

Phe Arg Ser Ser Asn Lys Tyr Ser Ser
            435                 440

<210> SEQ ID NO 11
<211> LENGTH: 444
<212> TYPE: PRT
<213> ORGANISM: Xenopus protein

<400> SEQUENCE: 11

Met Ala Thr Val Ile Leu Phe Val Ala Trp Met Ala Cys Leu Met Val
1               5                   10                  15

Gly Val Cys Tyr Gln Glu Phe Gln Thr Gln Asn Phe Pro Asp Ile
            20                  25                  30

Ser Asn Pro Ser Gln Glu Leu Asn Gln Glu Pro Ala His Arg Ile Val
            35                  40                  45

Gln Leu Asp Ser Ile Gln Asn Asn Gly Ala Leu Asn Met Ser Thr Gly
            50                  55                  60

Asn Val Leu Asn Met Ser Pro Pro Pro Ser Pro Cys Leu Ser Arg
65                  70                  75                  80

Ala Lys Ile Arg His Ala Phe Lys Tyr Val Thr Thr Ile Leu Ser Cys
            85                  90                  95
```

-continued

```
Val Ile Phe Leu Val Gly Ile Val Gly Asn Ser Thr Leu Leu Arg Ile
                100                 105                 110
Ile Tyr Lys Asn Lys Cys Met Arg Asn Gly Pro Asn Val Leu Ile Ala
            115                 120                 125
Ser Leu Ala Leu Gly Asp Leu Phe Tyr Ile Leu Ile Ala Ile Pro Ile
        130                 135                 140
Ile Ser Ile Ser Phe Trp Leu Ser Thr Gly His Ser Glu Tyr Ile Tyr
145                 150                 155                 160
Gln Leu Val His Leu Tyr Arg Ala Arg Val Tyr Ser Leu Ser Leu Cys
                165                 170                 175
Ala Leu Ser Ile Asp Arg Tyr Arg Ala Val Ala Ser Trp Asn Arg Ile
            180                 185                 190
Arg Ser Ile Gly Ile Pro Val Arg Lys Ala Ile Glu Leu Thr Leu Ile
        195                 200                 205
Trp Ala Val Ala Ile Ile Val Ala Val Pro Glu Ala Ile Ala Phe Asn
210                 215                 220
Leu Val Glu Leu Asp Phe Arg Gly Gln Thr Ile Leu Val Cys Met Leu
225                 230                 235                 240
Pro Met Glu Gln Thr Ser Asp Phe Met Arg Phe Tyr Gln Glu Val Lys
                245                 250                 255
Val Trp Trp Leu Phe Gly Phe Tyr Phe Cys Leu Pro Leu Ala Cys Thr
            260                 265                 270
Gly Val Phe Tyr Thr Leu Met Ser Cys Glu Met Leu Ser Ile Lys Asn
        275                 280                 285
Gly Met Arg Ile Ala Leu Asn Asp His Met Lys Gln Arg Arg Glu Val
290                 295                 300
Ala Lys Thr Val Phe Cys Leu Val Val Ile Phe Ala Leu Cys Trp Leu
305                 310                 315                 320
Pro Leu His Val Ser Ser Ile Phe Val Arg Leu Ser Ala Thr Val Lys
                325                 330                 335
Arg Ala Cys Ile Leu Lys Asn Lys Arg Ser Cys Ile Met Ala Glu Ile
            340                 345                 350
Gln Thr Gly Val Asn Tyr Gln Leu Leu Met Val Met Asn Tyr Thr Gly
        355                 360                 365
Ile Asn Met Ala Ser Leu Asn Ser Cys Ile Gly Pro Val Ala Leu Tyr
370                 375                 380
Phe Val Ser Arg Lys Phe Lys Asn Cys Phe Gln Ser Cys Leu Cys Cys
385                 390                 395                 400
Trp Cys His Arg Pro Thr Leu Thr Ile Thr Pro Met Asp Glu Lys Gly
                405                 410                 415
Ser Gly Gly Lys Trp Lys Ala Asn Gly His Asp Leu Asp Leu Asp Arg
            420                 425                 430
Ser Ser Ser Arg Leu Ser Asn Lys Tyr Ser Ser Ser
        435                 440
```

<210> SEQ ID NO 12
<211> LENGTH: 384
<212> TYPE: PRT
<213> ORGANISM: Human protein

<400> SEQUENCE: 12

```
Met Ala Leu Asn Asp Cys Phe Leu Leu Asn Leu Glu Val Asp His Phe
1               5                   10                  15
Met His Cys Asn Ile Ser Ser His Ser Ala Asp Leu Pro Val Asn Asp
```

-continued

```
                 20                  25                  30
Asp Trp Ser His Pro Gly Ile Leu Tyr Val Ile Pro Ala Val Tyr Gly
                 35                  40                  45

Val Ile Ile Leu Ile Gly Leu Ile Gly Asn Ile Thr Leu Ile Lys Ile
 50                  55                  60

Phe Cys Thr Val Lys Ser Met Arg Asn Val Pro Asn Leu Phe Ile Ser
 65                  70                  75                  80

Ser Leu Ala Leu Gly Asp Leu Leu Leu Ile Thr Cys Ala Pro Val
                 85                  90                  95

Asp Ala Ser Arg Tyr Leu Ala Asp Arg Trp Leu Phe Gly Arg Ile Gly
                100                 105                 110

Cys Lys Leu Ile Pro Phe Ile Gln Leu Thr Ser Val Gly Val Ser Val
                115                 120                 125

Phe Thr Leu Thr Ala Leu Ser Ala Asp Arg Tyr Lys Ala Ile Val Arg
                130                 135                 140

Pro Met Asp Ile Gln Ala Ser His Ala Leu Met Lys Ile Cys Leu Lys
145                 150                 155                 160

Ala Ala Phe Ile Trp Ile Ile Ser Met Leu Leu Ala Ile Pro Glu Ala
                165                 170                 175

Val Phe Ser Asp Leu His Pro Phe His Glu Glu Ser Thr Asn Gln Thr
                180                 185                 190

Phe Ile Ser Cys Ala Pro Tyr Pro His Ser Asn Glu Leu His Pro Lys
                195                 200                 205

Ile His Ser Met Ala Ser Phe Leu Val Phe Tyr Val Ile Pro Leu Ser
                210                 215                 220

Ile Ile Ser Val Tyr Tyr Tyr Phe Ile Ala Lys Asn Leu Ile Gln Ser
225                 230                 235                 240

Ala Tyr Asn Leu Pro Val Glu Gly Asn Ile His Val Lys Lys Gln Ile
                245                 250                 255

Glu Ser Arg Lys Arg Leu Ala Lys Thr Val Leu Val Phe Val Gly Leu
                260                 265                 270

Phe Ala Phe Cys Trp Leu Pro Asn His Val Ile Tyr Leu Tyr Arg Ser
                275                 280                 285

Tyr His Tyr Ser Glu Val Asp Thr Ser Met Leu His Phe Val Thr Ser
                290                 295                 300

Ile Cys Ala Arg Leu Leu Ala Phe Thr Asn Ser Cys Val Asn Pro Phe
305                 310                 315                 320

Ala Leu Tyr Leu Leu Ser Lys Ser Phe Arg Lys Gln Phe Asn Thr Gln
                325                 330                 335

Leu Leu Cys Cys Gln Pro Gly Leu Ile Ile Arg Ser His Ser Thr Gly
                340                 345                 350

Arg Ser Thr Thr Cys Met Thr Ser Leu Lys Ser Thr Asn Pro Ser Val
                355                 360                 365

Ala Thr Phe Ser Leu Ile Asn Gly Asn Ile Cys His Glu Arg Tyr Val
                370                 375                 380

<210> SEQ ID NO 13
<211> LENGTH: 390
<212> TYPE: PRT
<213> ORGANISM: Rattus protein

<400> SEQUENCE: 13

Met Pro Pro Arg Ser Leu Pro Asn Leu Ser Leu Pro Thr Glu Ala Ser
1               5                   10                  15
```

-continued

```
Glu Ser Glu Leu Glu Pro Glu Val Trp Glu Asn Asp Phe Leu Pro Asp
             20                  25                  30

Ser Asp Gly Thr Thr Ala Glu Leu Val Ile Arg Cys Val Ile Pro Ser
         35                  40                  45

Leu Tyr Leu Ile Ile Ile Ser Val Gly Leu Leu Gly Asn Ile Met Leu
     50                  55                  60

Val Lys Ile Phe Leu Thr Asn Ser Thr Met Arg Ser Val Pro Asn Ile
 65                  70                  75                  80

Phe Ile Ser Asn Leu Ala Ala Gly Asp Leu Leu Leu Leu Leu Thr Cys
                 85                  90                  95

Val Pro Val Asp Ala Ser Arg Tyr Phe Phe Asp Glu Trp Val Phe Gly
            100                 105                 110

Lys Leu Gly Cys Lys Leu Ile Pro Ala Ile Gln Leu Thr Ser Val Gly
            115                 120                 125

Val Ser Val Phe Thr Leu Thr Ala Leu Ser Ala Asp Arg Tyr Arg Ala
130                 135                 140

Ile Val Asn Pro Met Asp Met Gln Thr Ser Gly Val Val Leu Trp Thr
145                 150                 155                 160

Ser Leu Lys Ala Val Gly Ile Trp Val Val Ser Val Leu Leu Ala Val
            165                 170                 175

Pro Glu Ala Val Phe Ser Glu Val Ala Arg Ile Gly Ser Ser Asp Asn
            180                 185                 190

Ser Ser Phe Thr Ala Cys Ile Pro Tyr Pro Gln Thr Asp Glu Leu His
            195                 200                 205

Pro Lys Ile His Ser Val Leu Ile Phe Leu Val Tyr Phe Leu Ile Pro
    210                 215                 220

Leu Val Ile Ile Ser Ile Tyr Tyr Tyr His Ile Ala Lys Thr Leu Ile
225                 230                 235                 240

Arg Ser Ala His Asn Leu Pro Gly Glu Tyr Asn Glu His Thr Lys Lys
                245                 250                 255

Gln Met Glu Thr Arg Lys Arg Leu Ala Lys Ile Val Leu Val Phe Val
            260                 265                 270

Gly Cys Phe Val Phe Cys Trp Phe Pro Asn His Ile Leu Tyr Leu Tyr
            275                 280                 285

Arg Ser Phe Asn Tyr Lys Glu Ile Asp Pro Ser Leu Gly His Met Ile
            290                 295                 300

Val Thr Leu Val Ala Arg Val Leu Ser Phe Ser Asn Ser Cys Val Asn
305                 310                 315                 320

Pro Phe Ala Leu Tyr Leu Leu Ser Glu Ser Phe Arg Lys His Phe Asn
                325                 330                 335

Ser Gln Leu Cys Cys Gly Gln Lys Ser Tyr Pro Glu Arg Ser Thr Ser
            340                 345                 350

Tyr Leu Leu Ser Ser Ser Ala Val Arg Met Thr Ser Leu Lys Ser Asn
            355                 360                 365

Ala Lys Asn Val Val Thr Asn Ser Val Leu Leu Asn Gly His Ser Thr
    370                 375                 380

Lys Gln Glu Ile Ala Leu
385                 390
```

HUMAN ENDOTHELIN-BOMBESIN RECEPTOR ANTIBODIES

CROSS REFERENCE TO RELATED APPLICATIONS

This application is a divisional of application Ser. No. 09/030,970, filed on Feb. 26, 1998 now U.S. Pat. No. 6,143,519 which is a divisional of application Ser. No. 08/465,687, filed on Jun. 6, 1995, now U.S. Pat. No. 5,750,370, issued on May 12, 1998, which is a continuation-in-part of International Application No. PCT/US94/11843, filed Oct. 17, 1994; priority to these applications is hereby claimed under 35 U.S.C. §120, and each of these applications is hereby incorporated by reference in its entirety.

INTRODUCTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor. The transmembrane receptor is a G-protein coupled receptor. More particularly, the 7-transmembrane receptor has been putatively identified as an endothelin-bombesin receptor, sometimes hereinafter referred to as "ETBR." The invention also relates to inhibiting the action of such polypeptides.

BACKGROUND OF THE INVENTION

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336: 783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The peptide endothelin is a peptide of 21 amino acid residues and performs in vivo effects via endothelin receptors. Endothelin (ET) is a peptide present in various tissues in animals and is known as a strong vasoconstrictor. ET is one peptide of a family of at least 4 mammalian peptides characterized by 2 disulphide bridges and 6 conserved amino acid residues at the C-terminus.

Members of the family are called endothelin-1 (ET-1), endothelin-2 (ET-2), and endothelin-3 (ET-3). A fourth peptide, vasointestinal contractor, is also sometimes described as the murine or rat form of ET-2. They differ mostly in the 29-membered ring system formed by the Cys-3-Cys-11 disulphide bond. Endothelins are produced by metabolism of a preproendothelin to a proendothelin, which is itself metabolized to the mature endothelin. The cleavage of proendothelin is thought to be due to the activity of a specific enzyme. ETs are distributed in a wide variety of vascular and non-vascular tissues (PNAS, USA, 86:2863–2867 (1989)).

It has previously been shown in vivo that ET-1 and ET-2 are much stronger vasoconstrictors than ET-3, whereas the three ET isopeptides are roughly equipotent in producing the transient vasodilation. The analysis of nucleic acid sequences of ETs has revealed that various kinds of ET isopeptides exist. These ET isopeptides are also different in their properties. Therefore, it appears that various sub-types of ET-receptors exist. The existence of various sub-types of ET-receptors has been proven by the radioactive ligand binding studies of Watanabe, H., et al., Biochem-Biophys, Res. Commun., 161: 1252–1259 (1989), and Martin, E. R., et al., J. Biol. Chem., 265:14044–14049 (1990). These studies indicate the existence of at least two kinds of ET-receptors. One of them has a higher affinity for ET-1 and ET-2 than for ET-3 and the other has an affinity for ET-1, ET-2 and ET-3 with no cell activity. The $ET_A$ receptors have a lower affinity for ET-3 and the $ET_B$ receptors are non-selective.

The receptors are homologous to other heptahelical receptors of the rhodopsin superfamily, having 7 hydrophobic regions predicted to form transmembrane helices.

The placenta has a very high expression of both receptors, as does the lung. In general the non-selective $ET_B$ receptor seems to be more widely expressed (e.g., in liver, kidney and uterus) and is probably the more prominent receptor in the CNS, a result that agrees with binding and functional studies. The heart is the only tissue about which there is a consensus that an $ET_A$-type receptor predominates. The $ET_A$ receptors are associated with blood vessels and $ET_B$ receptors with glial, epithelial and ependymal cells, but few, if any, are associated with neurons. In the kidney, $ET_A$ receptors are located on blood vessel smooth-muscle cells, and $ET_B$ receptor expression occurs on a glomerular endothelium, vasa recti and the thin segments of Henle's loops.

Endothelins elicit biological responses by various signal transduction mechanisms, including the G-protein-coupled activation of phospholipase C and the activation of voltage-dependent $Ca^{2+}$ channels (Kasuya, Y., et al., Biochem. Biophys. Res. Commun., 61:1049–1055 (1989)). Thus, different sub-types of the endothelin receptor may use different signal-transduction mechanisms. Endothelin receptors have a relatively long N terminus preceding transmembrane segment I, and this portion may be involved in binding a relatively large endothelin peptide.

BRIEF SUMMARY OF THE INVENTION

Applicants have discovered a G-protein coupled receptor which has hydropathicity and amino acid homology which shows the existence of the 7 hydrophobic segments and a significant sequence similarity with other G-protein-coupled receptors. The 7 membrane-spanning domains and extra-cellular N-terminus and cytoplasmic C-terminus have also been identified.

The G-protein coupled receptor of the present invention has been putatively identified as an endothelin-bombesin receptor as a result of its homology to the known endothelin receptors $ET_A$ and $ET_B$ and as a result of its ability to bind endothelin and bombesin.

In accordance with one aspect of the present invention, there is provided a novel putative mature polypeptide which is a G-protein coupled receptor, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, to measure the concentration of endothelin in vivo, or in soluble form as an antagonist.

In accordance with yet a further aspect of the present invention, there are provided antibodies against such polypeptides.

In accordance with yet another aspect of the present invention, there are provided antagonists to such polypeptides, which may be used to inhibit the action of such polypeptides.

In accordance with still another embodiment, there is provided a process for using the receptor to screen for receptor antagonists and/or receptor agonists and/or receptor ligands.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE FIGURES

FIGS. 1A–H show the cDNA sequence (SEQ ID NO:1) and the corresponding deduced amino acid sequence (SEQ ID NO:2) of the G-protein coupled receptor of the present invention. The first 26 amino acids represent a putative signal sequence. The standard one-letter abbreviation for amino acids is used.

Figure 3A2:
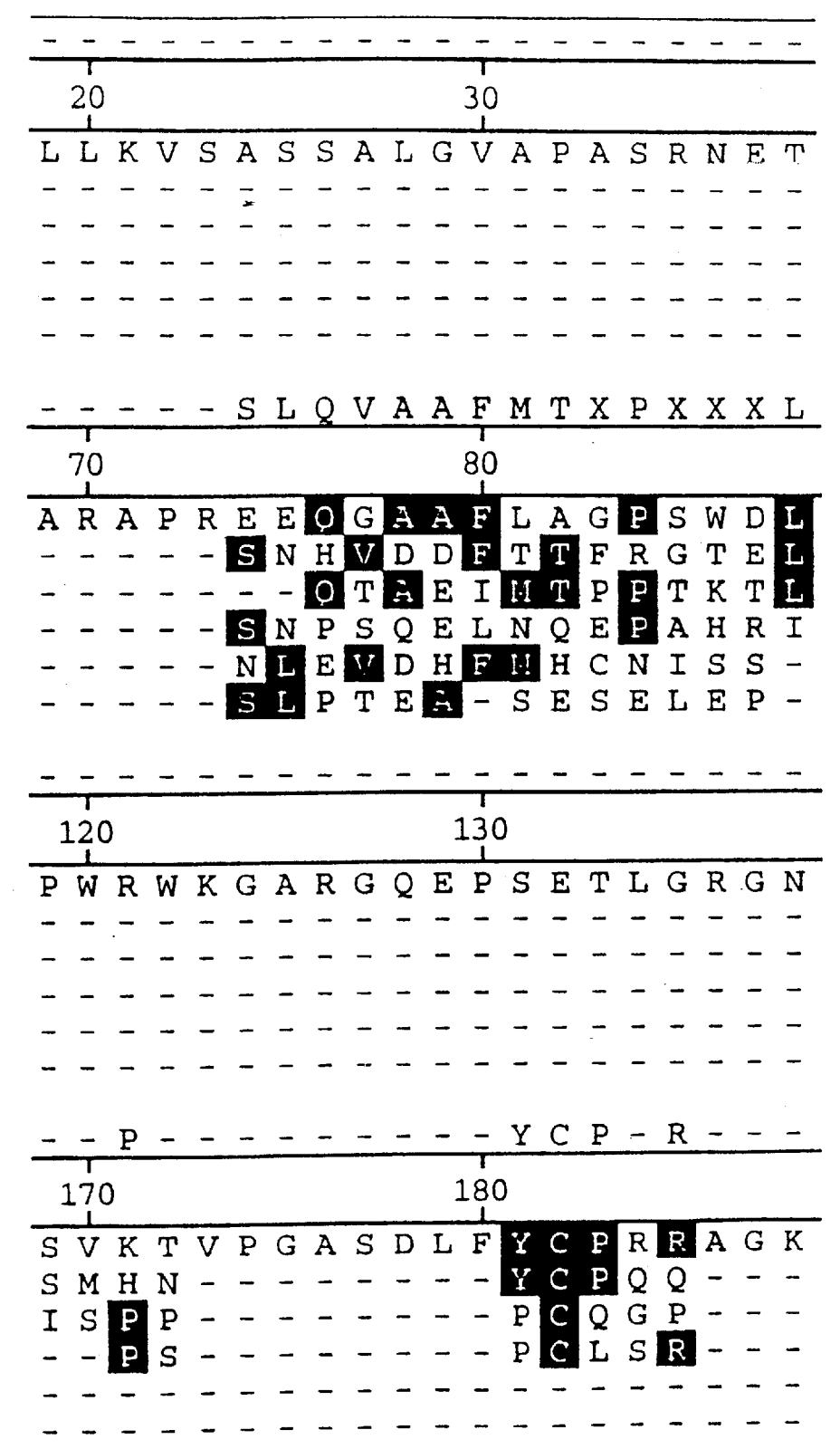
Figure 3B1:
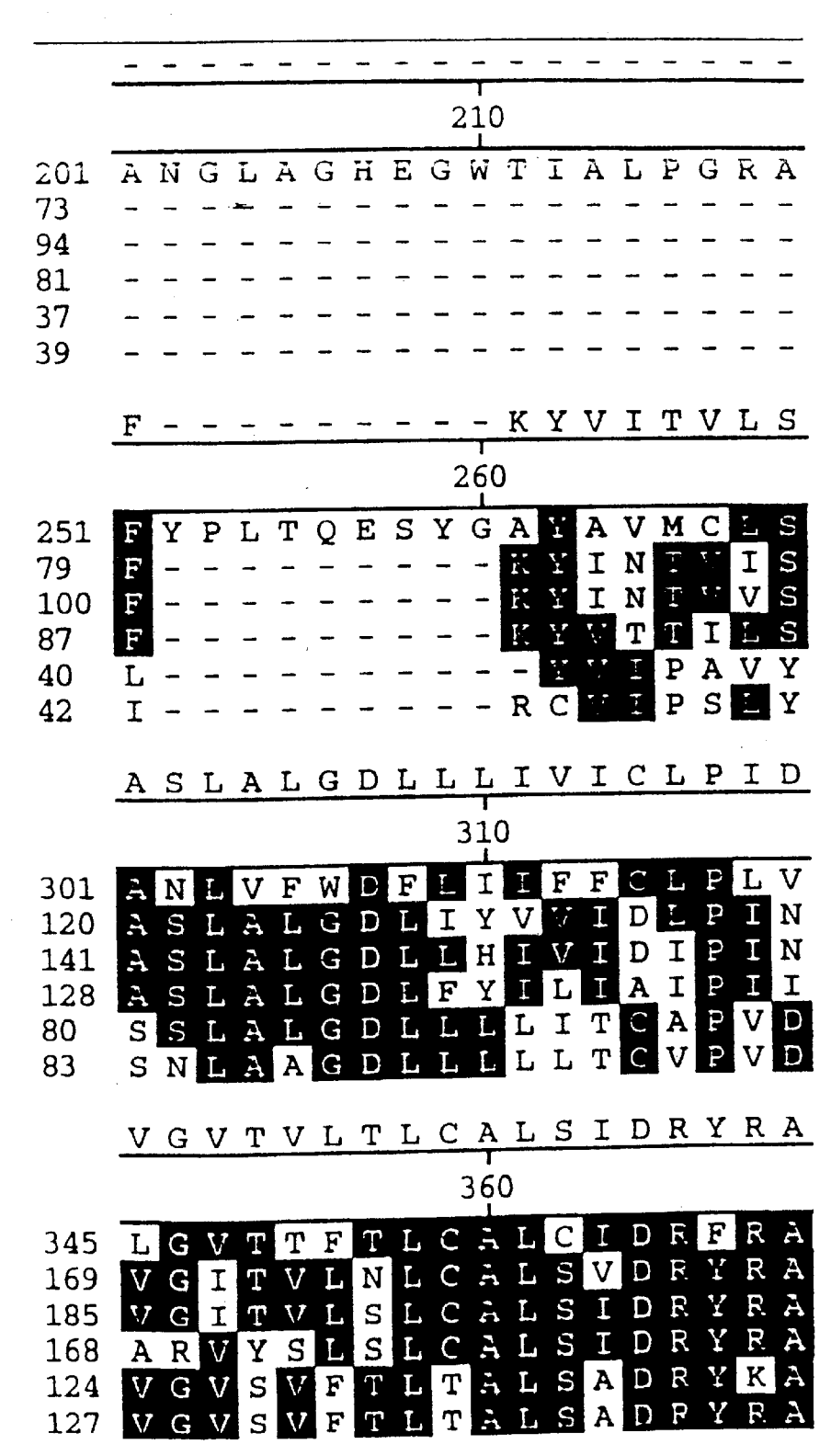
Figure 3B2:
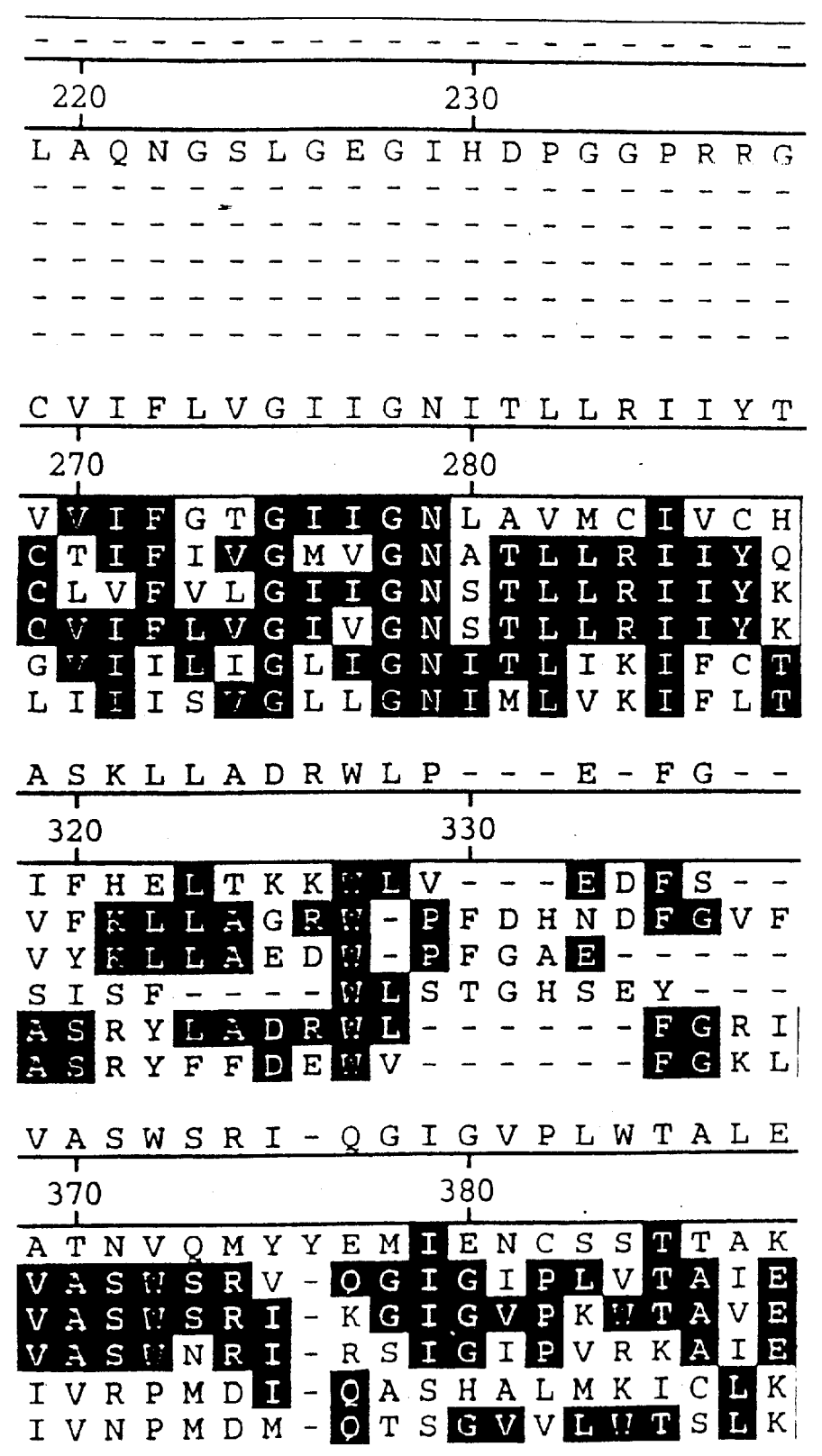
Figure 3C1:
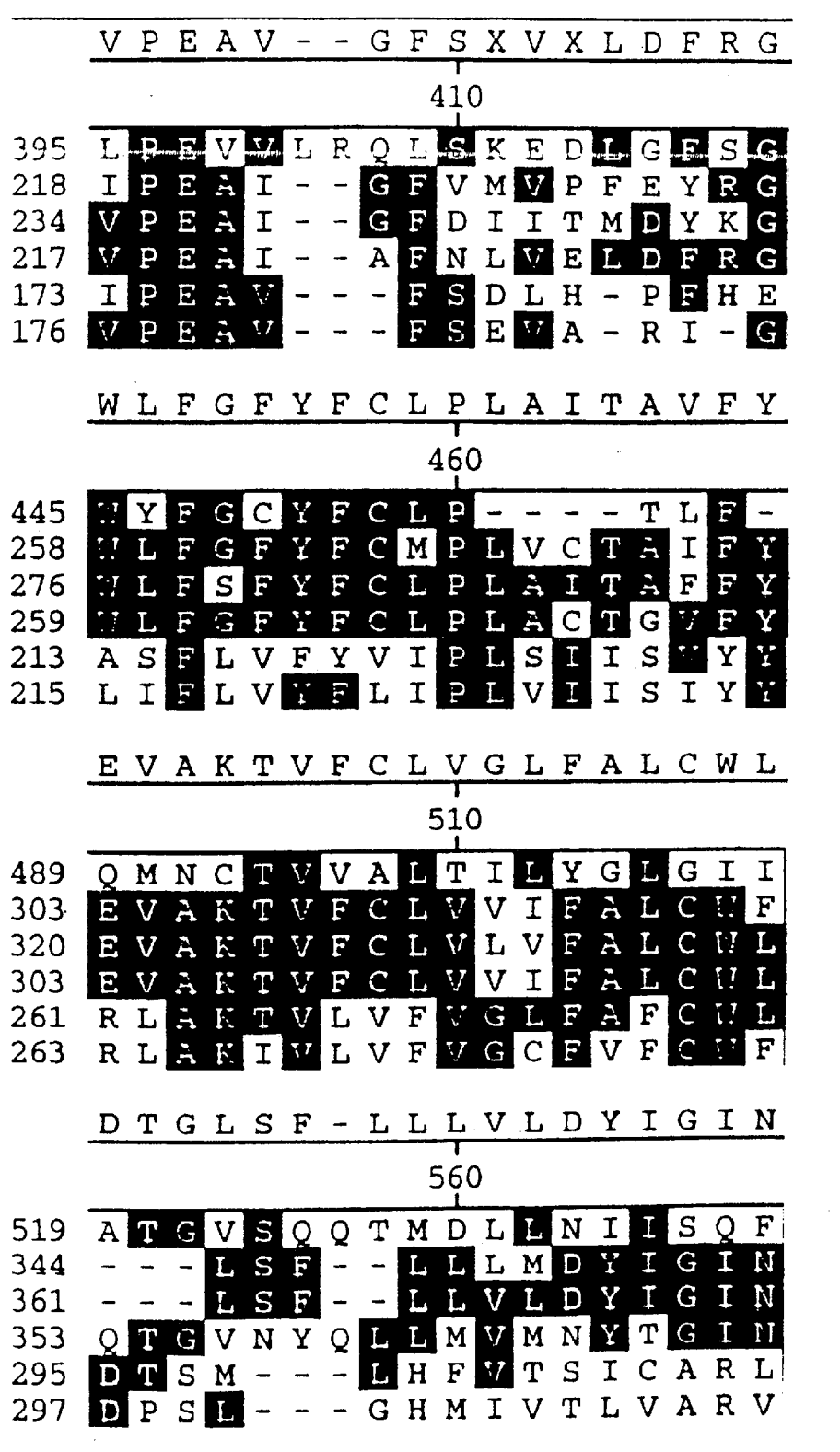
Figure 3C2:
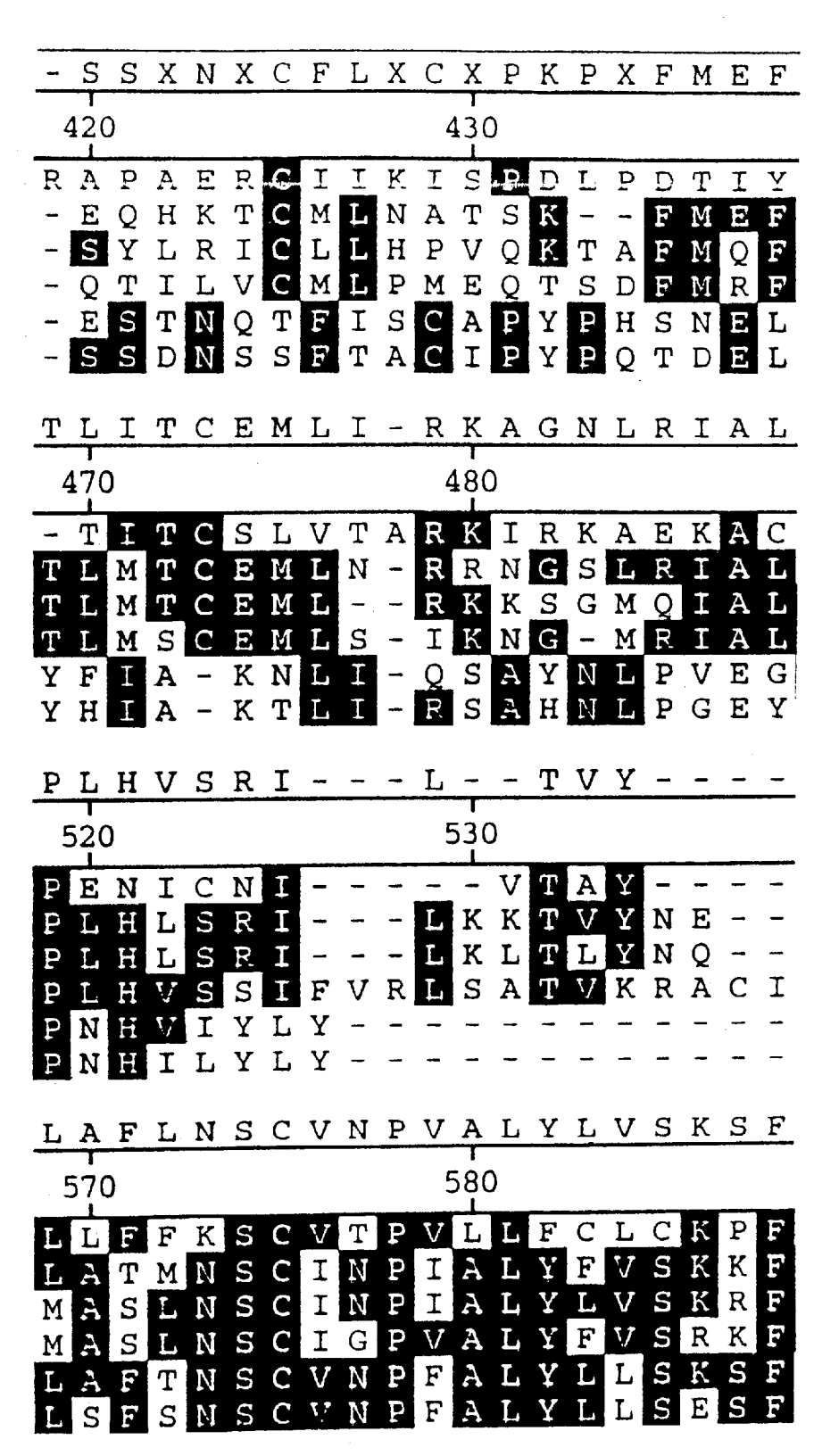
Figure 3D:
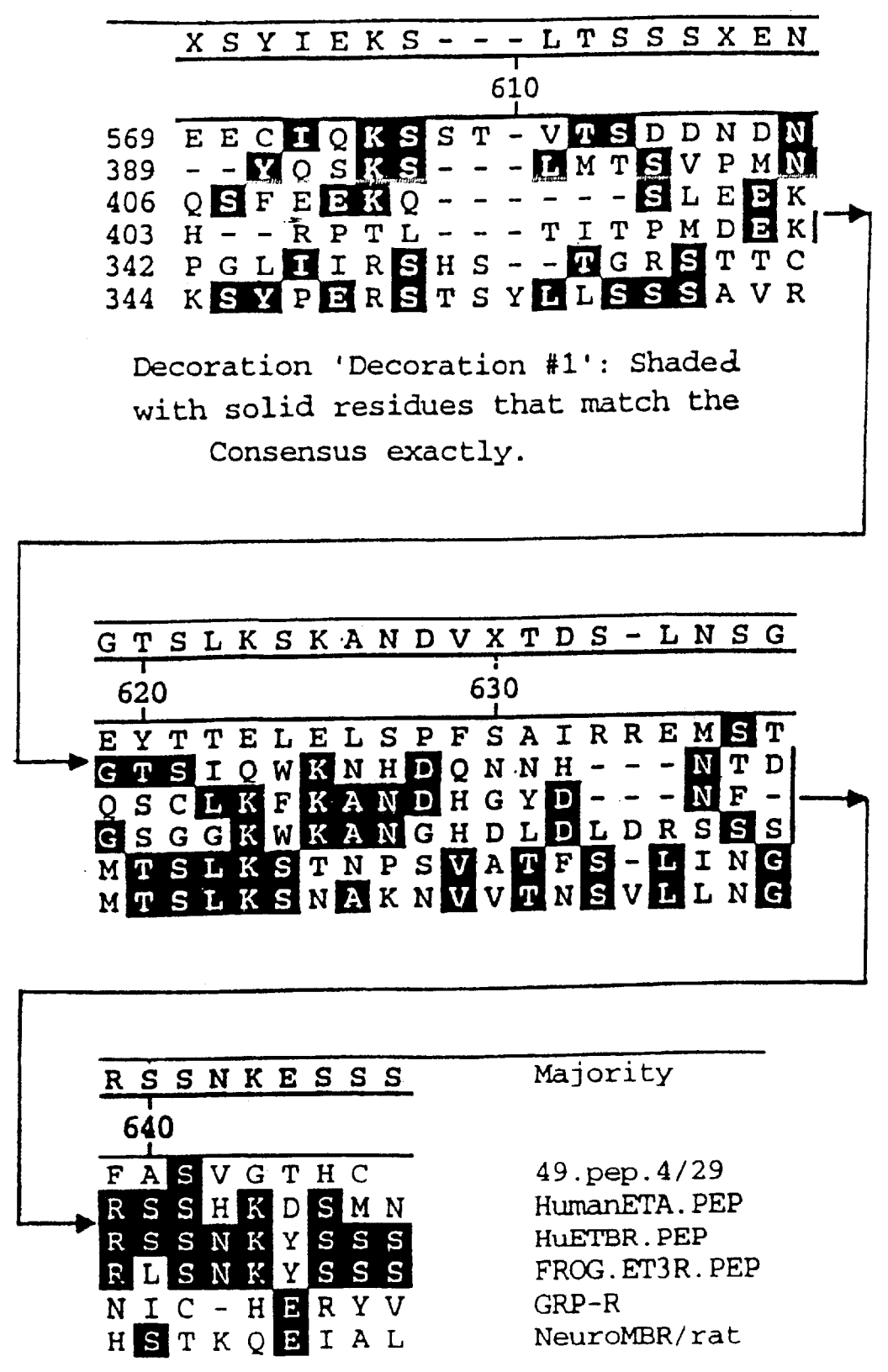

FIGS. 3A1–A3, 3B1–B3, 3C1–C3 and 3D illustrate an amino acid alignment of the G-protein coupled receptor of the present invention and endothelin receptors from various species of animals. Faded areas are those areas which match with the other amino acid sequences in the figure.

FIG. 4 shows that ET1, ET3 and Bombesin induced chloride currents in oocytes injected with pHHPEC49 derived RNA transcripts. The trace shows ET1 mediated chloride current (nanoamps). Arrow indicates ET1 addition. The inset shows the mean peak responses to 10 nM AII, Neuropeptide Y (NPY) and Bradykinin. The mean peak ± S.E. peak current response to ET1 is 150±50 (n=75), ET2 156±55 (n=75) and Bombesin 148±47 (n=75).

Figure 2A:
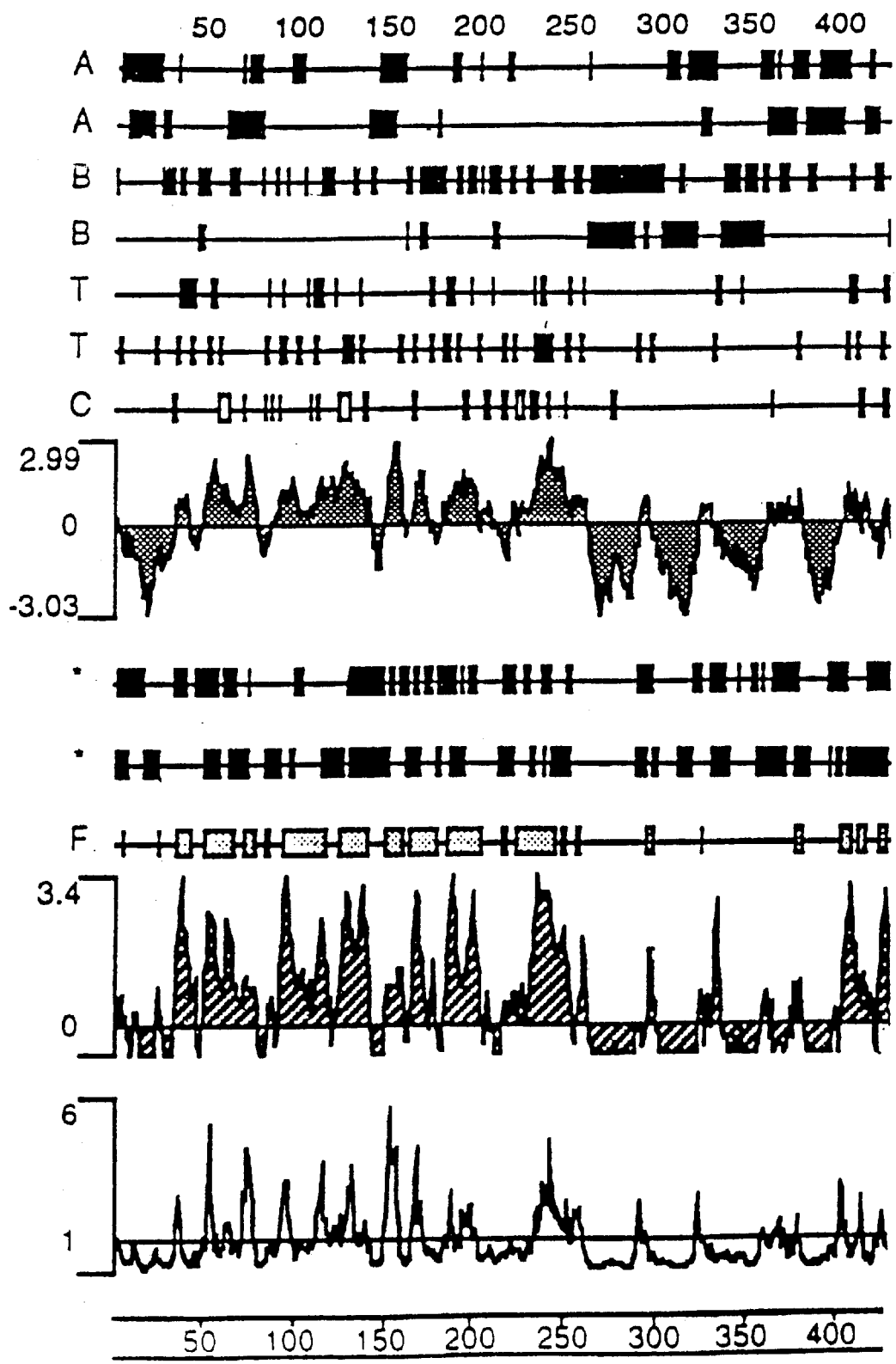
FIGS. 2A–B is an illustration of the secondary structural features of the G-protein coupled receptor. The first 7 illustrations set forth the regions of the amino acid sequence which are alpha helices, beta sheets, turn regions or coiled regions. The boxed areas are the areas which correspond to the region indicated. The second set of figures illustrate areas of the amino acid sequence which are exposed to intracellular, cytoplasmic or are membrane-spanning. The hydrophilicity part illustrates areas of the protein sequence which are the lipid bilayer of the membrane and are, therefore, hydrophobic, and areas outside the lipid bilayer membrane which are hydrophilic. The antigenic index corresponds to the hydrophilicity plot, since antigenic areas are areas outside the lipid bilayer membrane and are capable of binding antigens. The surface probability plot further corresponds to the antigenic index and the hydrophilicity plot. The amphipathic plots show those regions of the 13 sequences which are polar and non-polar. The flexible regions correspond to the second set of illustrations in the sense that flexible regions are those which are outside the membrane and inflexible regions are transmembrane regions.

It should be pointed out that sequencing inaccuracies are a common problem which occurs in polynucleotide sequences. Accordingly, the sequence of the drawing is based on several sequencing runs and the sequencing accuracy is considered to be at least 97%.

DETAILED DESCRIPTION OF THE INVENTION

In accordance with an aspect of the present invention, there is provided an isolated nucleic acid (polynucleotide) which encodes for the mature polypeptide having the deduced amino acid sequence of FIGS. 1A–H (SEQ ID NO:2) or for the mature polypeptide encoded by the cDNA of the clone deposited as with The American Type Culture Collection ("ATCC") on Jun. 24, 1994, and assigned ATCC Deposit No. 75823. The ATCC is located at 10801 University Boulevard, Manassas, Va. 20110-2209.

A polynucleotide encoding a polypeptide of the present invention may be found in brain, liver and placenta. The polynucleotide of this invention was discovered in a cDNA library derived from a human brain. It is structurally related to the G protein-coupled receptor family. It contains an open reading frame encoding a protein of about 613 amino acid residues of which approximately the first 26 amino acids residues are the putative leader sequence such that the mature protein comprises 587 amino acids. The protein exhibits the highest degree of homology to a human $ET_A$ receptor with 30% identity and 55% similarity over a 420 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding stand or non-coding (anti-sense) strand. The coding sequence which encodes the mature polypeptide may be identical to the coding sequence shown in FIGS. 1A–H (SEQ ID NO:1) or that of the deposited clone or may be a different coding sequence which coding sequence, as a result of the redundancy or degeneracy of the genetic code, encodes the same mature polypeptide as the DNA of FIGS. 1A–H (SEQ ID NO:1) or the deposited cDNA.

The polynucleotide which encodes for the mature polypeptide of FIGS. 1A–H (SEQ ID NO:2) or for the mature polypeptide encoded by the deposited cDNA may include: only the coding sequence of the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encoded for fragments, analogs and derivatives of the polypeptide having the deduced amino acid sequence of FIGS. 1A–H (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–H (SEQ ID NO:2) or the same mature polypeptide encoded by the cDNA of the deposited clone as well as variants of such polynucleotides which variants encode for a fragment, derivative or analog of the polypeptide of FIGS. 1A–H (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–H (SEQ ID NO:1) or of the coding sequence of the deposited clone. As known in the art, an allelic variant is an alternative form of a polynucleotide sequence which may have a substitution, deletion, or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of a protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequence (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at last 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides with either retain substantially the same biological function or activity as the mature polypeptide encode by the cDNAs of FIGS. 1A–H (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptides of SEQ ID NO:2 as well as fragments thereof, which fragments have at least 30 bases and preferably at least 50 bases and to polypeptides encoded by such polynucleotides. The deposit(s) referred to herein will be maintained under the terms of the Budapest Treaty on the International Recognition of the Deposit of Microorganisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use of sell the deposited materials, and no such license is hereby granted.

The present invention further relates to a G-protein coupled receptor polypeptide which has the deduced amino acid sequence of FIGS. 1A–H (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–H (SEQ ID NO:2)

or that encoded by the deposited cDNA, means a polypeptide which either retains substantially the same biological function or activity as such polypeptide, i.e., functions as a G-protein coupled receptor, or retains the ability to bind the ligand or the receptor even through the polypeptide does not function as a G-protein coupled receptor, for example, a soluble form of the receptor. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–H (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which are employed for purification of the mature polypeptide or a proprotein sequence or (v) one in which a fragment of the polypeptide is soluble, i.e., not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the ETBR genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli. lac* or *trp*, the phage lambda P$_l$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected form any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic an eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is included by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Bombesin, in addition to endothelin, has been found to bind to and stimulate the receptor of the present invention. Bombesin is a tetradecapeptide which has as a mammalian homolog the 27-amino acid peptide gastrin-releasing peptide (GRP). Bombesin is regarded as one of the most potent peptide to affect the central nervous system, since it has been reported as a thermoregulator in the rat (Brown, M. et al., Science, 196:998–1000 (1977)). Also, bombesin/gastrin releasing peptide is synthesized and secreted by small cell lung cancers (Davis, T. P. et al., Peptides, 13:401–17 (1992)).

The G-protein coupled receptor of the present invention may be employed in a process for screening for agonists and/or antagonists for the receptor.

In general, such screening procedures involve providing appropriate cells which express the receptor on the surface thereof. In particular, a polynucleotide encoding the receptor of the present invention is employed to transfect cells to thereby express the G-protein coupled receptor. Such transfection may be accomplished by procedures as hereinabove described.

One such screening procedure involves the use of a melanophore which are transfected to express the G-protein coupled receptor of the present invention. Such a screening technique is described in PCT WO 92/01810 published Feb. 6, 1992.

Thus, for example, such assay may be employed for screening for a receptor antagonist by contacting the melanophore cells which encode the G-protein coupled receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, potential agonists or antagonists may be contacted with a cell which expresses the G-protein coupled receptor and a second messenger response, e.g. signal transduction of pH changes, may be measured to determine whether the potential agonist or antagonist is effective.

another such screening technique involves introducing RNA encoding the G-protein coupled receptor into Xenopus oocytes to transiently express the receptor. The receptor oocytes may then be contacted with the receptor ligand and a compound to be screened, followed by detection of inhibition of a calcium signal.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a potential antagonist in the presence of a labeled form of a know ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

In general, antagonists for G-protein coupled receptors which are determined by such screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

Examples of potential antagonists includes an antibody, or in some cases an oligonucleotide, which binds to the G-protein coupled receptor but does not elicit a second messenger response such that the activity of the G-protein coupled receptor is prevented. Potential antagonists also include proteins which are closely related to the ligand of the G-protein coupled receptor, i.e a fragment of the ligand, which have lost biological function and when binding to the G-protein coupled receptor, elicit no response.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979): Cooney et al, Science 241:456 (1988); and Dervan et al., Science, 251:1360 (1991)), thereby preventing transcription and the production of G-protein coupled receptor. The antisense RNA oligonucleotide hybridizes to the mRNA in vivo and blocks translation of the mRNA molecule into the G-protein coupled receptor (antisense - Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

Another potential antagonist is a small molecule which binds to the G-protein coupled receptor, making it inaccessible to ligands such that normal biological activity is prevented. Examples of small molecules includes but are not limited to small peptides or peptide-like molecules.

Potential antagonists also include a soluble G-protein coupled receptor, e.g. a fragment of the receptor, which binds to the ligand and prevents the ligand from interacting with membrane bound G-protein coupled receptors.

An endothelin antagonists may be employed to offset the vasoconstrictive effects of endothelin and, therefore, may be employed to treat hypertension through vasodilation. These antagonists may also be used to treat the long-lasting vasospasms due to subarachnoid hemorrhages which cause increases in endothelin levels in cerebrospinal fluid and plasma.

Endothelin antagonists may also be employed to treat ulcerogenesis and gastric lesions. Et-1 and Et-3 induce gastric lesions and enhance alcohol-induced lesions. Accordingly, inhibiting ET-1 and ET-3 from interacting with the ETBRs can prevent these conditions.

Endothelins potently contract pulmonary smooth muscle and levels of endothelins are increased in pulmonary lavage fluid during asthmatic attacks, therefore, antagonists for diminishing or preventing binding of endothelin may be employed to treat asthma.

Endothelin levels are increased in cancer tissue and a cancer-derived cell line can be stimulated to produce endothelin. ET-1 itself stimulates growth of cancerous cells. Accordingly, endothelin antagonists may be employed to prevent the growth of cancer cells and tumors.

An increase in circulating endothelin levels is increased by ciclosporin, which may explain the toxic effects of ciclosporin. Accordingly, endothelin antagonists may be used to prevent and/or treat ciclosporin toxicity.

Endothelin antagonists may also be employed to treat septic shock which is caused by pathological levels of endothelins. Further, hypertension, congestive heart failure, coronary artery disease, atherosclerosis, restenosis, benign prostatic hypertrophy, renal failure and stroke may also be treated with the antagonists of ETBRs.

Bombesin antagonists may be employed to treat small cell lung cancers which synthesize and secret bombesin/gastrin releasing peptide. A bombesin antagonist will prevent bombesin from stimulating the ETBR of the present invention.

The antagonists may be employed in a composition with a pharmaceutically acceptable carriers, e.g., as hereinafter described.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonist and/or antagonists may also be employed for determining ligands which bind to the receptor.

the ETBR polypeptides and antagonists or agonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agent regulating the manufacture, use or sale of pharmaceuticals or biological products, which notice reflects approval by the agency of manufacture, use or sale for human administration. In addition, the polypeptides and agonists and antagonists may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The ETBR polypeptides and antagonists or agonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo, by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficieny virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7 No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form produce cell lines. Examples of packaging cells which may be transfected include, but are not limited to, the PE501, PA317, ψ-2, ψ-AM, PA12, T19-14X, VT-19-17-H2, ψCRE, ψCRIP, GP+E–86, GP+envAM12, and DAN cell lines are described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which includes the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

This invention also provides a method of detecting expression of a receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a receptor polypeptide of the present invention, by low stringency cross hybridization, or by identifying receptors that interact with related natural or synthetic ligands and or elicit similar behaviors after genetic or pharmacological blockage of the receptor polypeptides of the present invention.

The present invention also contemplates the use of the genes of the present invention as a diagnostic, for example, some diseases result from inherited defective genes. These genes can be detected by comparing the sequence of the defective gene with that of a normal one. Subsequently, one can verify that a "mutant" gene is associated with abnormal receptor activity. In addition, one can insert mutant receptor genes into a suitable vector for expression in a functional assay system (e.g., colorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention, Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA,* 85:4397–4401 1985).

In addition, some disease are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to receptor proteins. Unattached reporter antibody is then washed out. Peroxidase substrates are then added to the dish and the amount of color developed in a given time period is a measurement of the amount of receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCT mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA,* 85:4397–4401 1985). Such data are found, for example, in V. McKusick, Mendelian Inheritance in Man (available on line through John Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as FAB fragments, or the product of an Fab expression library. Various procedures known in the art maybe used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milestein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available. Publicly available on an unrestricted basis, or can be constructed from available plasmids in accord with published procedures. In addition, equivalents plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 Ig of plasmid or DNA fragment is used with about 2 units of enzyme in about 20 Il of buffer solution. For the purpose of isolating DNA fragments for plasmid construction, typically 5 to 50 Ig of DNA are digested with 20 to 250 units of enzyme in a larger volume. Appropriate buffers and substrate amounts for particular restriction enzymes are specific by the manufacturer. Incubation times of about 1 hour at 37° C. are ordinarily used, but may vary in accordance with the supplier's instructions. After digestion the reaction is electrophorsed directly on a polyacrylamide gel to isolate the desired fragment.

Size separation of the cleaved fragment sis performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 50' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of ETBR

The DNA sequence encoding for ETBR, ATCC # 75823, is initially amplified using PCR oligonucleotide primers corresponding to the 5' and sequences of the processed ETBR protein (minus the signal peptide sequence) and the vector sequences 3' to the ETBR gene. Additional nucleotides corresponding to ETBR were added to the 5' and 3' sequences respectively. The 5' oligonucleotide primer has the sequence 5' CACTAAGCTTAATGCGAGCCCCGGGCGCG 3' (SEQ ID NO:3) contains a HindIII restriction enzyme site followed by 18 nucleotides of ETBR coding sequence starting from the presumed terminal amino acid of the processed protein codon. The 3' sequence 5' GAACTTCTAGACCGTCAGCAATGAGTACCGAC 3' (SEQ ID NO:4) contains complementary sequences to an XbaI site and is followed by 18 nucleotides of ETBR. The restriction enzyme sites correspond to the restriction enzyme sites on the bacterial expression vector pQE-9 (Qiagen, Inc, 9259 Eton Avenue, Chatsworth, Calif., 91311). pQE-9 encodes antibiotic resistance ($Amp^r$), a bacterial original of replication (ori), an IPTG-regulatable promoter operator (P/O), a ribosome binding site (RBS), a 6-His tag and restriction enzyme sites. pQE-9 was then digested with HindIII and XbaI. The amplified sequences were ligated into pQE-9 and were inserted in frame with the sequence encoding for the histidine tag and the RBS. The ligation mixture was then used to transform E. coli, HB101 by the procedure described in Sambrook, J. et al., Molecular Cloning: A Laboratory Manual, Cold Spring Laboratory Press, (1989). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media and supplemented with both Amp (100 ug/ml) and Kan (25 ug/ml). The O/N culture is used to inoculate a large culture at a ratio of 1:100 to 1:250. The cells were grown to an optical density 600 ($O.D.^{600}$) of between 0.4 and 0.6 IPTG ("Isopropyl-B-D-thiogalacto pyranoside") was then added to a final concentration of 10 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized ETBR was purified from this solution by chromatography on a Nickel-Chelate column under conditions that allow for tight binding by proteins containing the 6-His tag (Hochuli, E, et al., J. Chromatography 411:177–181 (1984)). ETBR was eluted from the column in 60 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Expression of Recombinant ETBR in COS cells

The expression of plasmid, pETBR HA is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire ETBR protein and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for ETBR, ATCC # 75823, was constructed by PCR on the original EST cloned using two primers: the 5' primer 5' GTCCAAGCTTGCCACCAT-GCGAGCCCCGGGCGCG 3' (SEQ ID NO:5) contains an HindIII site followed by 18 nucleotides of ETBR coding sequence starting from the initiation codon; the 3' sequence 5' CTAGCTCGAGTCAAGCGTAGTCTGG-GACGTCGTATGGGTAGCAGCAAT GAGTTCCGA-CAGA 3' (SEQ ID NO:6) contains complementary sequences to an XhoI site, translation stop codon, HA tag and the last 18 nucleotides of the ETBR coding sequence (not including the stop codon). Therefore, the PCR product contains a HindIII site, ETBR coding sequence followed by HA tag fused in frame, a translation termination stop codon next to the HA tag, and an XhoI site. The PCT amplified DNA fragment and the vector, pcDNAI/Amp, were digested with HindIII and XhoI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant ETBR, COS cells were transfected with the expression vector by DEAE-DEXTRAN method (J. Sambrook, E. Fritsch, T. Maniatas, Molecular Cloning: A Laboratory Manual, Cold Spring Laboratory Pres, (1989)). The expression of the ETBR HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson I, et al., Id. 37:767 (1984)). Both cell lysate and culture media were precipitated with a HA specific monoclonal antibody. Proteins precipitated were analyzed on 15% SDS-PAGE gels.

EXAMPLE 3

Cloning and Expression of ETBR Using the Baculovirus Express System

The DNA sequence encoding the full length ETBR protein, ATCC # 75823, amplified using PCR oligonucleotide primers corresponding to the 5' and 3' sequences of the gene:

The 5' primer has the sequence 5' CGGGATCCGCCAC-CATGCGAGC CCCGGGCGCG 3' (SEQ ID NO:7) and contains a BamHI restriction enzyme site (in bold) followed by 6 nucleotides resembling an efficient signal for the initiation of translation in eukaryotic cells (J. Mol. Biol, 1987, 196, 947–950, Kozak, M.), and just behind, is the first 18 nucleotides of the ETBR gene (the initiation codon for translation "ATG" is underlined).

The 3' primer has the sequence 5' CGGGATCCCGCT-CAGCAA TGAGTTCCGAC 3' (SEQ ID NO:8) and contains the cleavage site for the restriction endonuclease BamHI and 18 nucleotides complementary to the 3' non-translated sequence of the ETBR gene. The amplified sequences were isolated from a 1% agarose gel using a commercially available kit ("Geneclean," BIO 101 Inc., La Jolla, Calif.). The fragment was then digested with the endonucleases BamHI and then purified again on a 1% agarose gel. This fragment is designated F2.

The vector pRG1 (modification of pVL941 vector, discussed below) is used for the expression of the ETBR protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases BamHI. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-medicated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restricted enzymes BamHI and then dephosphorylated using calf intestinal phosphatase by procedures known in the art. The DNA was then isolated from a 1% agarose gel. This vector DNA is designated V2.

Fragment F2 and the dephosphorylated plasmid V2 were ligated with T4 DNA ligase. *E.coli* HB101 cells were then transformed and bacteria identified that contained the plasmid (pBacETBR) with the ETBR gene using the enzymes BamHI. The sequence of the cloned fragment was confirmed by DNA sequencing.

5 $\mu$g of the plasmid pBacETBR were cotransfected with 1.0 $\mu$g of a commercially available linearized baculovirus ("BaculoGold™ baculovirus DNA", Pharmingen, San Diego, Calif.) using the lipofection method (Felgner et al. Proc. Natl. Acad. Sci. U.S.A., 84:7413–7417 (1987).

1 $\mu$g of BaculoGold™ virus DNA and 5 $\mu$g of the plasmid pBacETBR were mixed in a sterile well of a microtiter plate containing 50 $\mu$l of serum free Grace's medium (Life Technologies Inc., Gaithersburg, Md.). Afterwards 10 $\mu$l Lipofectin plus 90 $\mu$l Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-ETBR at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 4

*Xenopus oocyte* Assay to Identify Ligand

RNA was synthesized in vitro from linearized DNA, ATCC #75823, using an RNA transcription kit. This RNA was microinjected into *Xenopus oocytes* (10 ng of RNA/occytes). The *oocytes* were manually defolliculated prior to microinjection to remove any endogenous receptors that might be present in the follicular membranes. The injected *oocytes* were maintained in modified Barth's medium at 18° C. for 48 hours to allow for receptor protein expression. Electrophysiology was performed using the voltage-clamp technique. *Oocytes* were clamped at −60 mV and the calcium activated chloride channel activity was recorded in Barth's medium at room temperature. Data were analyzed using Axotape software.

As shown in FIG. 4, *oocytes* injected with the synthetic RNA complementary to DNA from ATCC #75823, illicited fairly strong Cl⁻ currents upon addition of 10 nM ET1, ET3 as well as Bombesin. Addition of ET1, ET3 and Bombesin to uninjected *oocytes* on the other hand did not elicit any change in membrane potential (data not shown). The ET1 and ET3 mediated response was blocked by the ET receptor peptide antagonist BQ123. Addition of related peptide ligands like AII, Neuropeptide Y and Bradykinin did not illicit any response (FIG. 4). This indicates that the ETBR is functional and is capable of coupling to a second messenger system which leads to the mobilization of intercellular stores of calcium via production of inositol triphosphate. Since it responds to both ET and Bombesin it represents a novel endothelin-bombesin receptor.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which corresponds to the 5' and 3' end sequences respectively. The 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated antibody or portion thereof that specifically binds to a protein selected from the group consisting of:
   (a) a protein whose sequence consists of amino acid residues 1 to 613 of SEQ ID NO:2;
   (b) a protein consisting of a fragment of SEQ ID NO:2, wherein said fragment comprises at least 30 contiguous amino acid residues of SEQ ID NO:2, and
   (c) a protein consisting of a fragment of SEQ ID NO:2, wherein said fragment comprises at least 50 contiguous amino acid residues of SEQ ID NO:2.

2. The antibody or portion thereof of claim 1 that specifically binds protein (a).

3. The antibody or portion thereof of claim 1 that specifically binds protein (b).

4. The antibody or portion thereof of claim 1 that specifically binds protein (c).

5. The antibody or portion thereof of claim 1 wherein said protein specifically bonded by said antibody or portion thereof is glycosylated.

6. The antibody or portion thereof of claim 1 which is a monoclonal antibody.

7. A hybridoma that produces the antibody of claim 6.

8. The antibody or portion thereof of claim 1 which is a polyclonal antibody.

9. The antibody or portion thereof of claim 1 which is a chimeric antibody.

10. The antibody or portion thereof of claim 1 which is a humanized antibody.

11. The antibody or portion thereof of claim 1 which is a human antibody.

12. The antibody or portion thereof of claim 1 which is a single chain antibody.

13. The antibody or portion thereof of claim 1 which is a Fab fragment.

14. The antibody or portion thereof of claim 1 which is labeled.

15. The antibody of claim 14 wherein the label is selected from the group consisting of:
   (a) an enzyme label;
   (b) a radioisotope; and
   (c) a fluorescent label.

16. A composition comprising the antibody or portion thereof of claim 1 and a carrier.

17. The composition of claim 16, wherein the antibody or portion thereof is a monoclonal antibody.

18. The composition of claim 16, wherein the antibody or portion thereof is a chimeric antibody.

19. The composition of claim 16, wherein the antibody or portion thereof is a humanized antibody.

20. The composition of claim 16, wherein the antibody or portion thereof is a human antibody.

21. The composition of claim 16, wherein the antibody or portion thereof is a single chain antibody.

22. The composition of claim 16, wherein the antibody or portion thereof is a Fab fragment.

23. The composition of claim 16, wherein the antibody or portion thereof is labeled.

24. The composition of claim 23 wherein the label is selected from the group consisting of:
   (a) an enzyme label;
   (b) a radioisotope; and
   (c) a fluorescent label.

25. An isolated cell that produces the antibody of claim 1.

26. A hybridoma that produces the antibody of claim 1.

27. A method of detecting endothelin-bombesin receptor (ETBR) protein in a biological sample comprising:
   (a) contacting the biological sample with the antibody or ETBR-binding portion thereof of claim 1, under conditions that allow formation of an antibody/ETBR protein complex; and
   (b) detecting the complex.

28. The method of claim 27 wherein the antibody is a monoclonal antibody.

29. The method of claim 27 wherein the antibody is a polyclonal antibody.

30. The method of claim 27 wherein the antibody is a chimeric antibody.

31. The method of claim 27 wherein the antibody is a humanized antibody.

32. The method of claim 27 wherein the antibody is a human antibody.

33. The method of claim 27 wherein the antibody is a single chain antibody.

34. The method of claim 27 wherein the antibody is a labeled antibody.

35. The method of claim 34 wherein the label is selected from the group consisting of:
   (a) an enzyme label;
   (b) a radioisotope; and
   (c) a fluorescent label.

36. An isolated antibody or portion thereof produced by immunizing an animal with a protein selected from the group consisting of:
   (a) a protein whose sequence comprises amino acid residues 1 to 613 of SEQ ID NO:2;
   (b) a protein whose sequence comprises at least 30 contiguous amino acid residues of SEQ ID NO:2; and
   (c) a protein whose sequence comprises at least 50 contiguous amino acid residues of SEQ ID NO:2,
   wherein said antibody or portion thereof specifically binds to said amino acid residues.

37. The antibody or portion thereof of claim 36 produced by immunizing an animal with protein (a).

38. The antibody or portion thereof of claim 36 produced by immunizing an animal with protein (b).

39. The antibody or portion thereof of claim 36 produced by immunizing an animal with protein (c).

40. An isolated antibody or portion thereof that specifically binds to a protein whose sequence consists of amino acid residues 27 to 613 of SEQ ID NO:2.

41. The antibody or portion thereof of claim 40 wherein said protein specifically bound by said antibody or portion thereof is glycosylated.

42. The antibody or portion thereof of claim 40 which is a monoclonal antibody.

43. A hybridoma that produces the antibody of claim 42.

44. The antibody or portion thereof of claim 40 which is a polyclonal antibody.

45. The antibody or portion thereof of claim 40 which is a chimeric antibody.

46. The antibody or portion thereof of claim 40 which is a humanized antibody.

47. The antibody or portion thereof of claim 40 which is a human antibody.

48. The antibody or portion thereof of claim 40 which is a single chain antibody.

49. The antibody or portion thereof of claim 40 which is a Fab fragment.

50. The antibody or portion thereof of claim 40 which is labeled.

51. The antibody or claim 50 wherein the label is selected from the group consisting of:
(a) an enzyme label;
(b) a radioisotope; and
(c) a fluorescent label.

52. A composition comprising the antibody or portion thereof of claim 40 and a carrier.

53. The composition of claim 52, wherein the antibody or portion thereof is a monoclonal antibody.

54. The composition of claim 52, wherein the antibody or portion thereof is a chimeric antibody.

55. The composition of claim 52, wherein the antibody or portion thereof is a humanized antibody.

56. The composition of claim 52, wherein the antibody or portion thereof is a human antibody.

57. The composition of claim 52, wherein the antibody or portion thereof is a single chain antibody.

58. The composition of claim 52, wherein the antibody or portion thereof is a Fab fragment.

59. The composition of claim 52, wherein the antibody or portion thereof is labeled.

60. The composition of claim 59 wherein the label is selected from the group consisting of:
(a) an enzyme label;
(b) a radioisotope; and
(c) a fluorescent label.

61. An isolated cell that produces the antibody of claim 60.

62. A hybridoma that produces the antibody of claim 60.

63. A method of detecting ETBR protein in a biological sample comprising:
(a) contacting the biological sample with the antibody or ETBR-binding portion thereof of claim 46, under conditions that allow formation of an antibody/ETBR protein complex; and
(b) detecting the complex.

64. The method of claim 63 wherein the antibody is a monoclonal antibody.

65. The method of claim 63 wherein the antibody is a polyclonal antibody.

66. The method of claim 63 wherein the antibody is a chimeric antibody.

67. The method of claim 63 wherein the antibody is a humanized antibody.

68. The method of claim 63 wherein the antibody is a human antibody.

69. The method of claim 63 wherein the antibody is a single chain antibody.

70. The method of claim 63 wherein the antibody is a labeled antibody.

71. The method of claim 70 wherein the label is selected from the group consisting of:
(a) an enzyme label;
(b) a radioisotope; and
(c) a fluorescent label.

72. An isolated antibody or portion thereof produced by immunizing an animal with a protein whose sequence comprises amino acid residues 27 to 613 of SEQ ID NO:2, wherein said antibody or portion thereof specifically binds to a protein consisting of amino acid residues 27 to 613 of SEQ ID NO:2.

73. An isolated antibody or portion thereof that specifically binds to a protein selected from the group consisting of:
(a) a protein whose sequence consists of the amino acid sequence of the polypeptide encoded by the cDNA contained in ATCC Deposit Number 75823;
(b) a protein consisting of a fragment of the polypeptide encoded by the cDNA contained in ATCC Deposit Number 75823, wherein said fragment comprises at least 30 contiguous amino acid residues of the polypeptide encoded by the cDNA contained in ATCC Deposit Number 75823; and
(c) a protein consisting of a fragment of the polypeptide encoded by the cDNA contained in ATCC Deposit Number 75823, wherein said fragment comprises at least 50 contiguous amino acid residues of the polypeptide encoded by the cDNA contained in ATCC Deposit Number 75823.

74. The antibody or portion thereof of claim 73 that specifically binds protein (a).

75. The antibody or portion thereof of claim 73 that specifically binds protein (b).

76. The antibody or portion thereof of claim 73 that specifically binds protein (c).

77. The antibody or portion thereof of claim 73 wherein said protein specifically bound by said antibody or portion thereof is glycosylated.

78. The antibody or portion thereof of claim 73 which is monoclonal antibody.

79. A hybridoma that produces the antibody of claim 78.

80. The antibody or portion thereof of claim 73 which is a polyclonal antibody.

81. The antibody or portion thereof of claim 73 which is a chimeric antibody.

82. The antibody or portion thereof of claim 73 which is a humanized antibody.

83. The antibody or portion thereof of claim 73 which is a human antibody.

84. The antibody or portion thereof of claim 73 which is a single chain antibody.

85. The antibody or portion thereof of claim 73 which is a Fab fragment.

86. The antibody or portion thereof of claim 73 which is labeled.

87. The antibody of claim 86 wherein the label is selected from the group consisting of:
(a) an enzyme label;
(b) a radioisotope; and
(c) a fluorescent label.

88. A composition comprising the antibody or portion thereof of claim 73 and a carrier.

89. The composition of claim 88, wherein the antibody or portion thereof is a monoclonal antibody.

90. The composition of claim 88, wherein the antibody or portion thereof is a chimeric antibody.

91. The composition of claim 88, wherein the antibody or portion thereof is a humanized antibody.

92. The composition of claim 88, wherein the antibody or portion thereof is a human antibody.

93. The composition of claim 88, wherein the antibody or portion thereof is a single chain antibody.

94. The composition of claim 88, wherein the antibody or portion thereof is a Fab fragment.

95. The composition of claim 88, wherein the antibody or portion thereof is labeled.

96. The composition of claim 95 wherein the label is selected from the group consisting of:
(a) an enzyme label;
(b) a radioisotope; and
(c) a fluorescent label.

97. An isolated cell that produces the antibody of claim 73.

98. A hybridoma that produces the antibody of claim 73.

99. A method of detecting ETBR protein in a biological sample comprising:
(a) contacting the biological sample with the antibody or ETBR-binding portion thereof of claim 73, under conditions that allow formation of an antibody/ETBR protein complex; and
(b) detecting the complex.

100. The method of claim 99 wherein the antibody is a monoclonal antibody.

101. The method of claim 99 wherein the antibody is a polyclonal antibody.

102. The method of claim 99 wherein the antibody is a chimeric antibody.

103. The method of claim 99 wherein the antibody is a humanized antibody.

104. The method of claim 99 wherein the antibody is a human antibody.

105. The method of claim 99 wherein the antibody is a single chain antibody.

106. The method of claim 99 wherein the antibody is a labeled antibody.

107. The method of claim 106 wherein the label is selected from the group consisting of:
(a) an enzyme label;
(b) a radioisotope; and
(c) a fluorescent label.

108. An isolated antibody or portion thereof produced by immunizing an animal with a protein selected from the group consisting of:
(a) a protein whose sequence comprises the amino acid sequence of the polypeptide encoded by the cDNA contained in ATCC Deposit Number 75823;
(b) a protein whose sequence comprises at least 30 contiguous amino acid residues of the polypeptide encoded by the cDNA contained in ATCC Deposit Number 75823; and
(c) a protein whose sequence comprises at least 50 contiguous amino acid residues of the polypeptide encoded by the cDNA contained in ATCC Deposit Number 75823;
wherein said antibody or portion thereof specifically binds to said polypeptide.

109. The antibody or portion thereof of claim 108 produced by immunizing an animal with protein (a).

110. The antibody or portion thereof of claim 108 produced by immunizing an animal with protein (b).

111. The antibody or portion thereof of claim 108 produced by immunizing an animal with protein (c).

112. An isolated antibody or portion thereof that specifically binds to a protein expressed on the surface of a cell comprising the cDNA contained in ATCC Deposit Number 75823, wherein said protein is encoded by said cDNA.

113. The antibody or portion thereof of claim 112 wherein said protein specifically bound by said antibody or portion thereof is glycosylated.

114. The antibody or portion thereof of claim 112 which is a monoclonal antibody.

115. A hybridoma that produces the antibody of claim 114.

116. The antibody or portion thereof of claim 112 which is a polyclonal antibody.

117. The antibody or portion thereof of claim 112 which is a chimeric antibody.

118. The antibody or portion thereof of claim 112 which is a humanized antibody.

119. The antibody or portion thereof of claim 112 which is a human antibody.

120. The antibody or portion thereof of claim 112 which is a single chain antibody.

121. The antibody or portion thereof of claim 112 which is a Fab fragment.

122. The antibody or portion thereof of claim 112 which is labeled.

123. The antibody or claim 122 wherein the label is selected from the group consisting of:
(a) an enzyme label;
(b) a radioisotope; and
(c) a fluorescent label.

124. A composition comprising the antibody or portion thereof of claim 112 and a carrier.

125. The composition of claim 124, wherein the antibody or portion thereof is a monoclonal antibody.

126. The composition of claim 124, wherein the antibody or portion thereof is a chimeric antibody.

127. The composition of claim 124, wherein the antibody or portion thereof is a humanized antibody.

128. The composition of claim 124, wherein the antibody or portion thereof is a human antibody.

129. The composition of claim 124, wherein the antibody or portion thereof is a single chain antibody.

130. The composition of claim 124, wherein the antibody or portion thereof is a Fab fragment.

131. The composition of claim 124, wherein the antibody or portion thereof is labeled.

132. The composition of claim 131 wherein the label is selected from the group consisting of:
(a) an enzyme label;
(b) a radioisotope; and
(c) a fluorescent label.

133. An isolated cell that produces the antibody of claim 112.

134. A hybridoma that produces the antibody of claim 112.

135. A method of detecting ETBR protein in a biological sample comprising:
(a) contacting the biological sample with the antibody or ETBR-binding portion thereof of claim 112, under conditions that allow formation of an antibody/ETBR protein complex; and
(b) detecting the complex.

136. The method of claim 135 wherein the antibody is a monoclonal antibody.

137. The method of claim 135 wherein the antibody is a polyclonal antibody.

138. The method of claim 135 wherein the antibody is a chimeric antibody.

139. The method of claim 135 wherein the antibody is a humanized antibody.

140. The method of claim 135 wherein the antibody is a human antibody.

141. The method of claim 135 wherein the antibody is a single chain antibody.

142. The method of claim 135 wherein the antibody is a labeled antibody.

143. The method of claim 142 wherein the label is selected from the group consisting of:
(a) an enzyme label;
(b) a radioisotope; and
(c) a fluorescent label.

144. An isolated antibody or portion thereof produced by immunizing an animal with a protein whose sequence comprises the amino acid sequence of the mature polypeptide encoded by the cDNA contained in ATCC Deposit Number 75823; wherein said antibody or portion thereof specifically binds to said polypeptide.

* * * * *

UNITED STATES PATENT AND TRADEMARK OFFICE
CERTIFICATE OF CORRECTION

PATENT NO.     : 6,518,404 B1
DATED          : February 11, 2003
INVENTOR(S)    : Li et al.

It is certified that error appears in the above-identified patent and that said Letters Patent is hereby corrected as shown below:

<u>Title page,</u>
Item [57], ABSTRACT, second line after the phrase "DNA (RNA) encoding such polypeptide and a procedure for", the phrase -- producing such polypeptide by recombinant techniques is -- should be inserted.

Figure 2B:
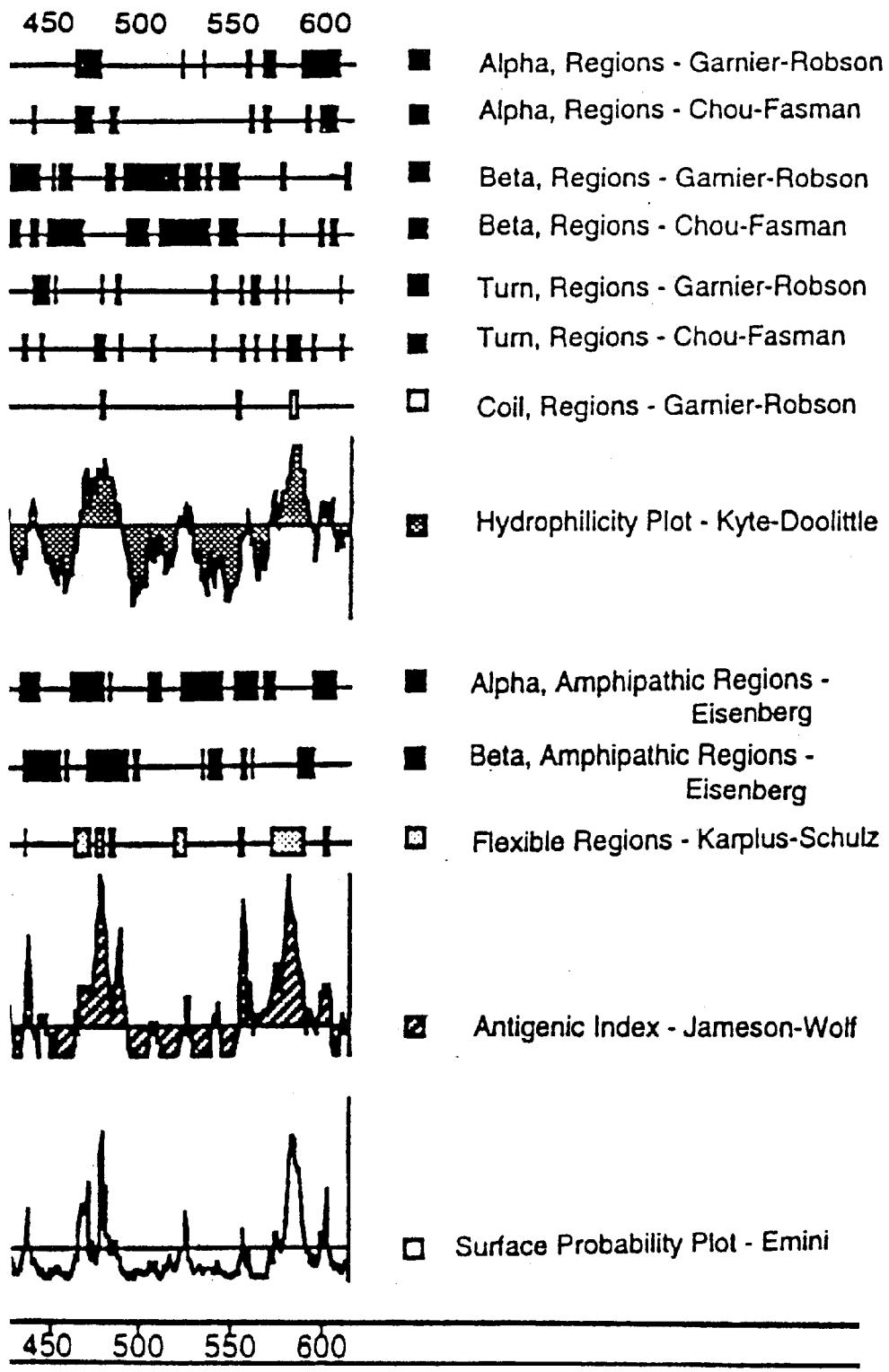

<u>Column 3,</u>
Line 46, "FIGS. 2A-B is" should read -- FIGS. 2A-B are --.

<u>Column 16, line 66 through Column 18, line 10,</u>
All text should be deleted.

<u>Column 19,</u>
Lines 26 and 29, each occurrence of "Ig", should read -- microgram --
Line 27, "Il" should read -- microliter --

Signed and Sealed this

Twenty-fourth Day of June, 2003

JAMES E. ROGAN
*Director of the United States Patent and Trademark Office*